US012752090B2

(12) United States Patent
Riccardi et al.

(10) Patent No.: US 12,752,090 B2
(45) Date of Patent: Oct. 6, 2026

(54) SYSTEM AND METHOD FOR CONTROLLING CSF FLOW AND MANAGING INTRACRANIAL PRESSURE

(71) Applicant: EnClear Therapies, Inc., Newburyport, MA (US)

(72) Inventors: Gianna N. Riccardi, South Berwick, ME (US); William X Siopes, Jr., Lowell, MA (US); Marcie Glicksman, Salem, MA (US); Anthony DePasqua, Newburyport, MA (US); Kevin Kalish, Newburyport, MA (US); Rajan Patel, Somerville, MA (US)

(73) Assignee: EnClear Therapies, Inc., Newburyport, MA (US)

( * ) Notice: Subject to any disclaimer, the term of this patent is extended or adjusted under 35 U.S.C. 154(b) by 104 days.

(21) Appl. No.: 17/495,682

(22) Filed: Oct. 6, 2021

(65) Prior Publication Data

US 2022/0105322 A1 Apr. 7, 2022

Related U.S. Application Data

(60) Provisional application No. 63/088,401, filed on Oct. 6, 2020.

(51) Int. Cl.
*A61M 27/00* (2006.01)

(52) U.S. Cl.
CPC ....... *A61M 27/006* (2013.01); *A61M 2205/18* (2013.01); *A61M 2205/3334* (2013.01)

(58) Field of Classification Search
CPC ............ A61M 27/006; A61M 2205/18; A61M 2205/3334; A61M 25/003; A61B 5/407;
(Continued)

(56) References Cited

U.S. PATENT DOCUMENTS

| | | | |
|---|---|---|---|
| 3,929,992 A | 12/1975 | Sehgal et al. | |
| 4,316,885 A | 2/1982 | Rakhit | |

(Continued)

FOREIGN PATENT DOCUMENTS

| | | |
|---|---|---|
| EP | 1481697 A1 | 12/2004 |
| EP | 1731182 A1 | 12/2006 |

(Continued)

OTHER PUBLICATIONS

Abbott, N., et al., "The role of brain barriers in fluid movement in the CNS: is there a 'glymphatic' system?" Acta Neuropathologica vol. 135, 2018, pp. 387-407.

(Continued)

*Primary Examiner* — Rebecca E Eisenberg
*Assistant Examiner* — Timothy L Flynn
(74) *Attorney, Agent, or Firm* — Nutter McClennen & Fish LLP

(57) ABSTRACT

A CSF management method and/or apparatus is used with a patient forms a CSF circuit having at least one pump and catheter. The CSF circuit is configured to control the flow of CSF in the patient's body. The method then flows, using the pump and the catheter, the patient's CSF at a given flow rate through the CSF circuit, and monitors, using a pressure sensor, the intracranial pressure in the craniospinal compartment of the patient when flowing CSF through the CSF circuit. For safety purposes, the method controls the given flow rate of the CSF in the CSF circuit as a function of the monitored intracranial pressure in the craniospinal compartment.

8 Claims, 11 Drawing Sheets

*CSF Circuit*

(58) Field of Classification Search
CPC ....... A61B 5/021; A61B 5/7275; A61B 5/026; A61B 5/14542; A61B 5/14546; A61B 5/4064; A61B 5/4839; A61B 5/031; G16H 20/40; G16H 50/30; G16H 50/20
See application file for complete search history.

(56) References Cited

U.S. PATENT DOCUMENTS

| | | | |
|---|---|---|---|
| 4,366,241 | A | 12/1982 | Tom et al. |
| 4,376,110 | A | 3/1983 | David et al. |
| 4,382,445 | A | 5/1983 | Sommers |
| 4,517,288 | A | 5/1985 | Giegel et al. |
| 4,650,803 | A | 3/1987 | Stella et al. |
| 4,655,745 | A | 4/1987 | Corbett |
| 4,830,849 | A | 5/1989 | Osterholm |
| 4,837,168 | A | 6/1989 | de Jaeger et al. |
| 4,950,232 | A | 8/1990 | Ruzicka et al. |
| 5,023,263 | A | 6/1991 | Von Burg |
| 5,023,264 | A | 6/1991 | Caufield et al. |
| 5,100,883 | A | 3/1992 | Schiehser |
| 5,118,677 | A | 6/1992 | Caufield |
| 5,118,678 | A | 6/1992 | Kao et al. |
| 5,120,842 | A | 6/1992 | Failli et al. |
| 5,130,307 | A | 7/1992 | Failli et al. |
| 5,162,333 | A | 11/1992 | Failli et al. |
| 5,177,203 | A | 1/1993 | Failli et al. |
| 5,221,670 | A | 6/1993 | Caufield |
| 5,233,036 | A | 8/1993 | Hughes |
| 5,256,790 | A | 10/1993 | Nelson |
| 5,258,389 | A | 11/1993 | Goulet et al. |
| 5,260,300 | A | 11/1993 | Hu |
| 5,262,423 | A | 11/1993 | Kao |
| 5,302,584 | A | 4/1994 | Kao et al. |
| 5,362,718 | A | 11/1994 | Skotnicki et al. |
| 5,373,014 | A | 12/1994 | Failli et al. |
| 5,378,836 | A | 1/1995 | Kao et al. |
| 5,385,908 | A | 1/1995 | Nelson et al. |
| 5,385,909 | A | 1/1995 | Nelson et al. |
| 5,385,910 | A | 1/1995 | Ocain et al. |
| 5,389,639 | A | 2/1995 | Failli et al. |
| 5,391,730 | A | 2/1995 | Skotnicki et al. |
| 5,405,316 | A | 4/1995 | Magram |
| 5,411,967 | A | 5/1995 | Kao et al. |
| 5,434,260 | A | 7/1995 | Skotnicki et al. |
| 5,463,048 | A | 10/1995 | Skotnicki et al. |
| 5,470,318 | A | 11/1995 | Griffith, III et al. |
| 5,480,988 | A | 1/1996 | Failli et al. |
| 5,480,989 | A | 1/1996 | Kao et al. |
| 5,489,680 | A | 2/1996 | Failli et al. |
| 5,491,231 | A | 2/1996 | Nelson et al. |
| 5,504,091 | A | 4/1996 | Molnar-Kimber et al. |
| 5,531,673 | A | 7/1996 | Helenowski |
| 5,563,145 | A | 10/1996 | Failli et al. |
| 5,665,772 | A | 9/1997 | Cottens et al. |
| 5,780,462 | A | 7/1998 | Lee et al. |
| 5,957,912 | A | 9/1999 | Heitzmann |
| 6,193,691 | B1 | 2/2001 | Beardsley |
| 6,210,346 | B1 | 4/2001 | Hall et al. |
| 6,273,913 | B1 | 8/2001 | Wright et al. |
| 6,277,983 | B1 | 8/2001 | Shaw et al. |
| 6,358,969 | B1 | 3/2002 | Shelley et al. |
| 6,471,960 | B1 | 10/2002 | Anderson |
| 6,585,764 | B2 | 7/2003 | Wright et al. |
| 6,599,275 | B1 | 7/2003 | Fischer, Jr. |
| 6,670,168 | B1 | 12/2003 | Katz et al. |
| 6,689,085 | B1 | 2/2004 | Rubenstein et al. |
| 6,696,488 | B2 | 2/2004 | Wolfe et al. |
| 6,808,536 | B2 | 10/2004 | Wright et al. |
| 6,916,310 | B2 | 7/2005 | Sommerich |
| 7,025,739 | B2 | 4/2006 | Saul |
| 7,037,288 | B2 | 5/2006 | Rosenberg et al. |
| 7,331,940 | B2 | 2/2008 | Sommerich |
| 7,662,140 | B2 | 2/2010 | Heruth et al. |
| 7,717,871 | B2 | 5/2010 | Odland |
| 7,763,142 | B2 | 7/2010 | Watson |
| 7,887,503 | B2 | 2/2011 | Geiger |
| 8,088,091 | B2 | 1/2012 | Thomas et al. |
| 8,137,334 | B2 | 3/2012 | Heruth et al. |
| 8,206,334 | B2 | 6/2012 | Kralick et al. |
| 8,216,173 | B2 | 7/2012 | Dacey, Jr. et al. |
| 8,292,856 | B2 | 10/2012 | Bertrand et al. |
| 8,435,204 | B2 | 5/2013 | Lad et al. |
| 9,097,723 | B2 | 8/2015 | Fathollahi et al. |
| 9,138,537 | B2 | 9/2015 | Miesel |
| 9,220,424 | B2 | 12/2015 | Wilson et al. |
| 9,421,348 | B2 | 8/2016 | Lenihan et al. |
| 9,603,792 | B2 | 3/2017 | John |
| 9,629,987 | B2 | 4/2017 | Anand et al. |
| 9,682,193 | B2 | 6/2017 | Anand et al. |
| 9,687,670 | B2 | 6/2017 | Dacey, Jr. et al. |
| 9,744,338 | B2 | 8/2017 | East et al. |
| 9,770,180 | B2 | 9/2017 | Radojicic |
| 9,895,518 | B2 | 2/2018 | Lad et al. |
| 9,919,138 | B2 | 3/2018 | Lenihan et al. |
| 10,258,781 | B2 | 4/2019 | Choi et al. |
| 10,272,188 | B1 | 4/2019 | Geiger et al. |
| 10,441,770 | B2 | 10/2019 | Singh et al. |
| 10,549,035 | B2 | 2/2020 | Hayek |
| 10,653,713 | B2 | 5/2020 | Thakker et al. |
| 10,695,484 | B1 | 6/2020 | Radojicic |
| 10,864,323 | B2 | 12/2020 | Gerrans |
| 11,534,592 | B2 | 12/2022 | Singh et al. |
| 2002/0004580 | A1 | 1/2002 | Fueyo et al. |
| 2002/0025521 | A1 | 2/2002 | Lu et al. |
| 2003/0060436 | A1 | 3/2003 | Schneider |
| 2003/0135148 | A1 | 7/2003 | Dextradeur et al. |
| 2004/0068241 | A1 | 4/2004 | Fischer |
| 2004/0110250 | A1 | 6/2004 | Wischik et al. |
| 2004/0138153 | A1 | 7/2004 | Ramesh et al. |
| 2004/0185042 | A1 | 9/2004 | Scheiflinger et al. |
| 2004/0220510 | A1 | 11/2004 | Koullick et al. |
| 2004/0236309 | A1 | 11/2004 | Yang |
| 2006/0025726 | A1 | 2/2006 | Fischer et al. |
| 2006/0074388 | A1 | 4/2006 | Dextradeur et al. |
| 2006/0079740 | A1 | 4/2006 | Silver et al. |
| 2006/0264897 | A1 | 11/2006 | Lobl et al. |
| 2007/0167867 | A1 | 7/2007 | Wolf |
| 2007/0173787 | A1 | 7/2007 | Huang et al. |
| 2007/0243179 | A1 | 10/2007 | Elia |
| 2008/0082036 | A1 | 4/2008 | Trescony et al. |
| 2008/0242590 | A1 | 10/2008 | Andersson et al. |
| 2009/0131857 | A1 | 5/2009 | Geiger |
| 2010/0030196 | A1 | 2/2010 | Hildebrand et al. |
| 2010/0234792 | A1 | 9/2010 | Dacey, Jr. et al. |
| 2011/0033463 | A1 | 2/2011 | Thakker et al. |
| 2012/0238835 | A1 | 9/2012 | Hyde et al. |
| 2012/0238936 | A1 | 9/2012 | Hyde et al. |
| 2013/0197422 | A1 | 8/2013 | Browd et al. |
| 2013/0273203 | A1 | 10/2013 | Oestergaard et al. |
| 2014/0018257 | A1 | 1/2014 | Suga et al. |
| 2014/0206102 | A1 | 7/2014 | Petrucelli et al. |
| 2014/0276340 | A1* | 9/2014 | Ludin ................. A61M 27/002 604/9 |
| 2014/0303455 | A1 | 10/2014 | Shachar et al. |
| 2014/0377319 | A1 | 12/2014 | Leuthardt et al. |
| 2015/0005800 | A1 | 1/2015 | Anile |
| 2015/0094644 | A1 | 4/2015 | Lenihan et al. |
| 2015/0201882 | A1 | 7/2015 | Swoboda et al. |
| 2015/0374898 | A1 | 12/2015 | Fujieda et al. |
| 2016/0002627 | A1 | 1/2016 | Bennett et al. |
| 2016/0025747 | A1 | 1/2016 | Ranum et al. |
| 2016/0089521 | A1 | 3/2016 | Dragoon et al. |
| 2016/0183819 | A1 | 6/2016 | Burnett et al. |
| 2016/0361365 | A1 | 12/2016 | Lee et al. |
| 2017/0059586 | A1 | 3/2017 | Petrucelli et al. |
| 2017/0095649 | A1* | 4/2017 | Vase ................... A61M 27/006 |
| 2017/0137492 | A1 | 5/2017 | Looby |
| 2017/0157038 | A1 | 6/2017 | Peyman |
| 2017/0157374 | A1 | 6/2017 | Hedstrom et al. |
| 2017/0203084 | A1* | 7/2017 | Lad ..................... A61M 27/006 |
| 2017/0313687 | A1 | 11/2017 | Hendrickson et al. |
| 2018/0028746 | A1 | 2/2018 | Abrams et al. |
| 2018/0185058 | A1 | 7/2018 | Anand et al. |
| 2018/0371010 | A1 | 12/2018 | Vassylyev et al. |

(56) References Cited

U.S. PATENT DOCUMENTS

| | | | | |
|---|---|---|---|---|
| 2019/0009014 | A1 | 1/2019 | Chen et al. | |
| 2019/0048371 | A1 | 2/2019 | Basheer et al. | |
| 2019/0083303 | A1 | 3/2019 | Khanna | |
| 2019/0085336 | A1 | 3/2019 | Zhu et al. | |
| 2019/0089521 | A1 | 3/2019 | Coulthard et al. | |
| 2019/0290481 | A1* | 9/2019 | Martinez | A61M 5/44 |
| 2019/0317099 | A1 | 10/2019 | Halbert et al. | |
| 2020/0001059 | A1 | 1/2020 | Campbell et al. | |
| 2020/0046952 | A1 | 2/2020 | Vase | |
| 2020/0046953 | A1* | 2/2020 | Vase | G16H 50/20 |
| 2020/0046954 | A1 | 2/2020 | Lad et al. | |
| 2020/0324006 | A1 | 10/2020 | Paul et al. | |
| 2020/0330497 | A1 | 10/2020 | Marcotulli et al. | |
| 2021/0023293 | A1 | 1/2021 | DePasqua et al. | |
| 2021/0033620 | A1 | 2/2021 | Porter et al. | |
| 2021/0046473 | A1* | 2/2021 | Needham | B01L 3/5027 |
| 2021/0077016 | A1 | 3/2021 | Bodner | |
| 2021/0145944 | A1 | 5/2021 | Navia et al. | |
| 2021/0154276 | A1 | 5/2021 | Navia et al. | |
| 2021/0162173 | A1 | 6/2021 | Singh et al. | |
| 2021/0369941 | A1* | 12/2021 | Korshøj | A61M 1/777 |
| 2021/0379344 | A1* | 12/2021 | Hakim | A61B 5/6868 |
| 2022/0096743 | A1 | 3/2022 | Riccardi et al. | |
| 2022/0096744 | A1 | 3/2022 | Riccardi et al. | |
| 2022/0096745 | A1 | 3/2022 | Riccardi et al. | |
| 2022/0134076 | A1 | 5/2022 | Bodner | |
| 2022/0160947 | A1 | 5/2022 | DePasqua et al. | |
| 2022/0257854 | A1 | 8/2022 | Bodner et al. | |
| 2022/0313890 | A1 | 10/2022 | Riccardi et al. | |
| 2022/0355015 | A1 | 11/2022 | Patel et al. | |
| 2022/0370716 | A1 | 11/2022 | Martin et al. | |
| 2022/0379010 | A1 | 12/2022 | Martin et al. | |
| 2022/0401645 | A1 | 12/2022 | Morse et al. | |
| 2023/0001165 | A1 | 1/2023 | Bourouiba et al. | |
| 2023/0056486 | A1 | 2/2023 | Navia et al. | |

FOREIGN PATENT DOCUMENTS

| | | | |
|---|---|---|---|
| EP | 3294398 | A1 | 3/2018 |
| EP | 3833251 | A1 | 6/2021 |
| EP | 4030988 | A1 | 7/2022 |
| WO | 98/02441 | A2 | 1/1998 |
| WO | 99/13886 | A1 | 3/1999 |
| WO | 99/15530 | A1 | 4/1999 |
| WO | 2000/056335 | A1 | 9/2000 |
| WO | 01/14387 | A1 | 3/2001 |
| WO | 2001/039819 | A2 | 6/2001 |
| WO | 2003015710 | A2 | 2/2003 |
| WO | 03/057218 | A1 | 7/2003 |
| WO | 2003/015710 | A3 | 2/2004 |
| WO | 2004/058337 | A1 | 7/2004 |
| WO | 2004/091444 | A2 | 10/2004 |
| WO | 2008/105959 | A2 | 9/2008 |
| WO | 2010123558 | A1 | 10/2010 |
| WO | 2011114260 | A1 | 9/2011 |
| WO | 2014/159247 | A1 | 10/2014 |
| WO | 2015/049588 | A2 | 4/2015 |
| WO | 2014/124365 | A3 | 10/2015 |
| WO | 2016183123 | A1 | 11/2016 |
| WO | 2017096228 | A1 | 6/2017 |
| WO | 2018005621 | A1 | 1/2018 |
| WO | 2019028006 | A1 | 2/2019 |
| WO | 2019/100074 | A1 | 5/2019 |
| WO | 2020/023417 | A1 | 1/2020 |
| WO | 2020/023418 | A1 | 1/2020 |
| WO | 2020/033773 | A1 | 2/2020 |
| WO | 2020064875 | A1 | 4/2020 |
| WO | 2020/0149993 | A1 | 7/2020 |
| WO | 2020/210634 | A1 | 10/2020 |
| WO | 2021/055100 | A1 | 3/2021 |
| WO | 2022/173620 | A1 | 8/2022 |
| WO | 2022/246042 | A1 | 11/2022 |

OTHER PUBLICATIONS

Allen, J., et al., "Abstract 3483: Modeling circulating tumor cells in the peripheral blood and CSF of breast cancer patients," Cancer Research vol. 73, Issue 8, 2013, abstract only.

Allen, J., et al., "Abstract 5565: Circulating tumor cells in the peripheral blood and cerebrospinal fluid of patients with central nervous system metastases," Cancer Research vol. 72, Issue 8, 2012, abstract only.

Andersen, P., et al., "Clinical genetics of amyotrophic lateral sclerosis: what do we really know?" Nature Reviews Neurology, vol. 7, 2011, pp. 603-615.

Arai, T., et al., "Phosphorylated and cleaved TDP?43 in ALS, FTLD and other neurodegenerative disorders and in cellular models of TDP?43 proteinopathy," Neuropathology, vol. 30, 2010, pp. 170-181.

Arai, T., et al., "TDP-43 is a component of ubiquitin-positive tau-negative inclusions in frontotemporal lobar degeneration and amyotrophic lateral sclerosis," Biochemical and Biophysical Research Communications, vol. 351, Issue 3, 2006, pp. 602-611.

Arriagada, P., et al., "Neurofibrillary tangles but not senile plaques parallel duration and severity of Alzheimer's disease," Neurology 42, 1992, pp. 631-639.

Asai, D., et al., "Chapter 3 Making Monoclonal Antibodies," Methods in Cell Biology, vol. 37, 1993, pp. 57-74.

Bioline "Proteinase K" accessed from bioline.com on Jun. 22, 2021 (Year: 2013).

Brat, D., et al., "Tau?associated neuropathology in ganglion cell tumours increases with patient age but appears unrelated to ApoE genotype," Neuropathy and Applied Neurobiology, vol. 27, Issue 3, 2001, pp. 197-205.

Buee, L., et al., "Tau protein isoforms, phosphorylation and role in neurodegenerative disorders," Brain Research Reviews, vol. 33, Issue 1, 2000, pp. 95-130.

Chang, Y., et al., "The Glycine-Alanine Dipeptide Repeat from C9orf72 Hexanucleotide Expansions Forms Toxic Amyloids Possessing Cell-to-Cell Transmission Properties" Journal of Biological Chemistry, vol. 291, Issue 10, 2016, pp. 4903-4911.

Coatti, G., et al., "Pericytes Extended Survival of ALS SOD1 Mice and Induce the Expression of Antioxidant Enzymes in the Murine Model and in IPSCs Dervised Neuronal Cells from an ALS Patient," Stem Cell Reviews and Reports (2017) 13: 686-698.

De Souza, P., et al., "A biotechnology perspective of fungal proteases," Brazilian Journal of Microbiology, vol. 46, 2, 2015, pp. 337-346.

Dejesus-Hernandez, M., et al., "Expanded GGGGCC Hexanucleotide Repeat in Noncoding Region of C9ORF72 Causes Chromosome 9p-Linked FTD and ALS," Neuron, vol. 72, 2011, pp. 245-256.

Diamond, S., "Methods for mapping protease specificity," Current Opinion in Chemical Biology, vol. 11, Issue 1, 2007, pp. 46-51.

Evidente, V., et al., "Post-encephalitic parkinsonism,"Journal of Neurology, Neurosurgery & Psychiatry, vol. 63, Issue 1, 1998, pp. 5.

Extended European Search Report for European Application No. 19839881.0 dated Jun. 21, 2022, 9 pages.

Extended European Search Report for European Application No. 19840444.4 dated Jun. 28, 2022, 7 pages.

Finsterer, J., et al., "Liquorpheresis (CSF filtration) in familial amyotrophic lateral sclerosis," Spinal Cord, vol. 39, 1999, pp. 592-593.

Giannakopoulos, P., et al., Tangle and neuron numbers, but not amyloid load, predict cognitive status in Alzheimer's disease, Neurology, vol. 60, 2003, pp. 1495-1500.

Giordana, M., et al., "Dementia and cognitive impairment in amyotrophic lateral sclerosis: a review," Neurological Sciences, vol. 32, 2011, pp. 9-16.

Gomez-Isla, T., et al., Neuronal loss correlates with but exceeds neurofibrillary tangles in Alzheimer's disease, Annals of Neurology, vol. 41, 1997, pp. 17-24.

Grad, L., et al., "Prion-like activity of Cu/Zn superoxide dismutase: implications for amyotrophic lateral sclerosis," 8:1, 2014, pp. 33-41.

Graff-Radford, N., et al., "Frontotemporal dementia," Seminars in Neurology vol. 27, 2007, pp. 48-57.

(56) References Cited

OTHER PUBLICATIONS

Hasegawa, M., et al., "Molecular Dissection of TDP-43 Proteinopathies," Journal of Molecular Neuroscience, vol. 45, 2011, pp. 480-485.
Hasegawa, M., et al., "Phosphorylated TDP-43 in frontotemporal lobar degeneration and amyotrophic lateral sclerosis," Annals of Neurology, vol. 62, Issue 1, 2008, pp. 60-70.
Hersh, D., et al., "MR-guided transcranial focused ultrasound safely enhances interstitial dispersion of large polymeric nanoparticles in the living brain," PLOS ONE 13(2): e0192240, 2018, 19 pages.
Indivero, V., "Technique filters cancer where chemo can't reach: A new therapy may help cancer patients with malignant ce4lls near the spinal cord and in the brain," dated Jul. 30, 2013. Retrieved from the internet under https://news.psu.edu/story/282970/2013/07/30/research/technique-filters-cancer-where-chemo-cant-reach, 4 pages.
International Preliminary Report on Patentability for International Application No. PCT/US2019/042880, mailed Jan. 12, 2021 (8 pages).
International Preliminary Report on Patentability for International Application No. PCT/US2020/027683, mailed Oct. 21, 2021 (11 pages).
International Search Report and Written Opinion for International Application No. PCT/US2019/042879, mailed Oct. 8, 2019 (14 pages).
International Search Report and Written Opinion for International Application No. PCT/US2019/042880, mailed Oct. 16, 2019 (10 pages).
International Search Report and Written Opinion for International Application No. PCT/US2020/027683, mailed Aug. 6, 2020 (19 pages).
International Search Report and Written Opinion for International Application No. PCT/US2021/013458, mailed Jun. 9, 2021 (20 pages).
International Search Report and Written Opinion for International Application No. PCT/US2021/052735, mailed Feb. 11, 2022, 28 pages.
International Searching Authority, International Search Report for International Application No. PCT/US2022/037609, dated Oct. 26, 2022, together with the Written Opinion of the International Searching Authority, 8 pages.
International Searching Authority, International Search Report for International Application No. PCT/US22/34706, dated Oct. 18, 2022, together with the Written Opinion of the International Searching Authority, 8 pages.
Jessen, N., et al., "The Glymphatic System—A Beginner's Guide," Neurochemical Research, 2015, 40(2), pp. 2583-2599.
Kaufman, S., et al., "Prion-Like Propagatio of Protein Aggregation and Related Therapeutic Strategies," Neurotherapeutics, 10, 2013, pp. 371-382.
Kim Kwang Soo, et al., "Proteolytic Cleavage of Extracellular a-Synuclein by Plasmin: Implications for Parkinson Disease" Journal of Biological Chemistry, vol. 287, No. 30, Mar. 22, 2012, pp. 24862-24872.
Kopeikina, K., et al., "Soluble forms of tau are toxic in Alzheimer's disease," Translational Neuroscience 3(3), 2012, pp. 223-233.
Kouzehgarani, G., et al., "Harnessing cerebrospinal fluid circulation for drug delivery to brain tissues, Advanced Drug Delivery Reviews," 2021, vol. 173, pp. 20-59.
Lee, V., et al., "Neurodegenerative tauopathies," Annual Review of Neuroscience, vol. 24, 2001, pp. 1121-1159.
Legon, W., et al., "Transcranial focused ultrasound modulates the activity of primary somatosensory cortex in humans," Nature Neuroscience vol. 17, No. 2, 2014, pp. 322-329.
Lei, P., et al., "Tau protein: relevance to Parkinson's disease," The International Journal of Biochemistry & Cell Biology, vol. 42, Issue 11, 2010, pp. 1775-1778.
Lin, Z., et al., "Facile synthesis of enzyme—inorganic hybrid nanoflowers and their application as an immobilized trypsin reactor for highly efficient protein digestion." (Communication) RSC Adv., 2014, 4, 13888-13891.
Lipsman, N., et al., "Blood-brain barrier opening in Alzheimer's disease using MR-guided focused ultrasound," Nature Communications vol. 9, Article 2336, 2018, pp. 1-8.
Lomen-Hoerth, C., et al., "The overlap of amyotrophic lateral sclerosis and frontotemporal dementia," Neurology, vol. 59, 2002, pp. 1077-1079.
Martin, L., et al., "Post-translational modifications of tau protein: implications for Alzheimer's disease," Neurochemistry International, vol. 58, Issue 4, pp. 458-471.
International Search Report and Written Opinion for International Application No. PCT/US2021/053829 mailed Jan. 13, 2022. 19 pages.
Marx, S., et al., "Bench to Bedside: The Development of Rapamycin and Its Application to Stent Restenosis", Journal of the American Heart Association 104, 2001, pp. 852-855.
May, S., et al., "C9orf72 FTLD/ALS-associated Gly-Ala dipeptide repeat proteins cause neuronal toxicity and Unc119 sequestration," Acta Neuropathologica, vol. 128, 2014, pp. 485-503.
Mckee, A., et al., "The Neuropathology of Chronic Traumatic Encephalopathy," Brain Pathology 253), 2015, pp. 350-364.
Mcrae et al., Mapping the active sites of bovine thrombin, factor IXa, factor Xa, factor Xla, factor Xlla, plasma kallikrein, and trypsin with amino acid and peptide thioesters: development of new sensitive substrates. Biochemistry 1981, 20, 25, pp. 7196-7206.
Menendez-Gonzalez, M., et al., "Targeting Beta-Amyloid at the CSF: A New Therapeutic Strategy in Alzheimer's Disease," Frontiers in Aging Neuroscience, vol. 10, 2018, pp. 1-8.
Mori, K., et al., "The C9orf72 GGGGCC repeat is translated into aggregating dipeptide-repeat proteins in FTLD/ALS," Science, vol. 339, No. 6125, Feb. 7, 2013, pp. 1335-1338.
Narasimhan, S., et al., "Pathological Tau Strains from Human Brains Recapitulate the Diversity of Tauopathies in Nontransgenic Mouse Brain," The Jorunal of Neuroscience, vol. 37, Issue 47, 2017, pp. 11406-11423.
Neumann, M., et al., "Ubiquitinated TDP-43 in frontotemporal lobar degeneration and amyotrophic lateral sclerosis," Science, vol. 314, 2006, pp. 130-133.
Ohki, Y., et al., "Glycine-alanine dipeptide repeat protein contributes to toxicity in a zebrafish model of C9orf72 associated neurodegeneration," Molecular Neurodegeneration (2017) 12:6, pp. 1-11.
Ozcelik, A., et al., "Acoustic tweezers for the life sciences," Nature Methods vol. 15, 2018, pp. 1021-1028.
Paraskevas, G., et al., "The emerging TDP-43 proteinpathy" Neuroimmunol Neuroinflammation 5:17 (Year 2018).
Pardridge, W., et al., "CSF, blood-brain barrier, and brain drug delivery," Expert Opinion on Drug Delivery, vol. 13, 2016, pp. 1-13.
Patel, A., et al., "Identification and enumeration of circulating tumor cells in the cerebrospinal fluid of breast cancer patents with central nervous system metastases," Oncotarget, vol. 2, No. 10, 2011, pp. 752-760.
Paulson, H., et al., "Genetics of Dementia," Seminars in Neurology, vol. 31, pp. 449-360.
Phukan, J., et al., "Cognitive impairment in amyotrophic lateral sclerosis," The Lancet Neurology, vol. 6, Issue 11, pp. 994-1003.
Poreba, M., et al., "Current Strategies for Probing Substrate Specificity of Proteases," Current Medicinal Chemistry, vol. 17, Issue 33, 2010, pp. 3968-3995.
Quinn, J., et al., "Tau Proteolysis in the Pathogenesis of Tauopathies: Neurotoxic Fragments and Novel Biomarkers," Journal of Alzheimer's Disease, vol. 63, No. 1, 2018, pp. 13-33.
Reinhard, M., et al., "Blood-Brain Barrier Disruption By Low-Frequency Ultrasound," Stroke, vol. 37, 2006, pp. 1546-1548.
Renton, A., et al., "A Hexanucleotide Repeat Expansion in C9ORF72 Is the Cause of Chromosome 9p21-Linked ALS-FTD," Neuron, vol. 27, Issue 2, pp. 257-268.
Saido, T., et al., "Proteolytic Degradation of Amyloid 13-Protein" Cold Spring Harbor Perspectives in Medicine, vol. 2, No. 6, Jun. 1, 2012, pp. a006379-a006379.
Sonabend, A., et al., "Overcoming the Blood-Brain Barrier with an Implantable Ultrasound Device," Clinical Cancer Research, vol. 25, Issue 13, 2019, pp. 3750-3752.

(56) References Cited

OTHER PUBLICATIONS

Song, J., et al., "Investigation of standing wave formation in a human skull for a clinical prototype of a large-aperture, transcranial MR-guided Focused Ultrasound (MRgFUS) phased array: An experimental and simulation study," IEEE Transactions on Biomedical Engineering, vol. 59, Issue 2, 2012, pp. 435-444.
Spencer, B., et al., "Lentivirus Mediated Delivery of Neurosin Promotes Clearance of Wild-type a-Synuclein and Reduces the Pathology in an a-Synuclein Model of LBD", Molecular Therapy, vol. 21, No. 1, Jan. 1, 2013, pp. 31-41.
Steele, J., et al., "Progressive Supranuclear Palsy A Heterogeneous Degeneration Involving the Brain Stem, Basal Ganglia and Cerebellum With Vertical Gaze and Pseudobulbar Palsy, Nuchal Dystonia and Dementia," Arch Neurol. vol. 10, No. 4, 1964, pp. 333-359.
Takalo, M., et al., "Protein aggregation and degradation mechanisms in neurodegenerative diseases," American Journal of Neurodegenerative Disease, 2013; 2(1), pp. 1-14.
Tanji, K., et al., "Proteinase K-resistant a-synuclein is deposited in presynapses in human Lewy body disease and A53T a-synuclein transgenic mice," Acta Neuropathologica, Springer, Berlin, DE, vol. 120, No. 2, Mar. 26, 2010, pp. 145-154.
Tarasoff-Conway, J., et al., "Clearance systems in the brain implications for Alzheimer disease," Nature Reviews Neurology 11(8), 2015, pp. 457-470.
Tyler, W., et al., "Remote Excitation of Neuronal Circuits Using Low-Intensity, Low-Frequency, Ultrasound," PLOS ONE vol. 3, Issue 10, 2008, e3511, 11 pages.
Westergard, T., et al., "Cell-to-Cell Transmission of Dipeptide Repeat Proteins Linked to C9orf72-ALS/FTD," Cell Reports, vol. 17, Issue 3, 2016, pp. 645-652.
Wray, S., et al., "Direct analysis of tau from PSP brain identifies new phosphorylation sites and a major fragment of N?terminally cleaved tau containing four microtubule?binding repeats," Journal of Neurochemistry, vol. 105, 2008, pp. 2343-2352.
Written Opinion of the International Preliminary Examining Authority for International Application No. PCT/US2019/042879, mailed Feb. 25, 2021 (6 pages).
Written Opinion of the International Preliminary Examining Authority for International Application No. PCT/US2019/042880, mailed Sep. 11, 2020 (8 pages).
Wszolek, Z., et al., "Frontotemporal dementia and parkinsonism linked to chromosome 17 (FTDP-17)" Orphanet Journal of Rare Diseases, 2006, 1:30, pp. 1-9.
Xie, L., et al., "Sleep Drives Metabolite Clearance from the Adult Brain," Science vol. 342, Issue 6156, 2013, pp. 373-377.
Zhang, Y., et al., "Aggregation-prone c9FTD/ALS poly(GA) RAN-translated proteins cause neurotoxicity by inducing ER stress," Acta Neuropathologica, vol. 128, 2014, pp. 504-524.

* cited by examiner

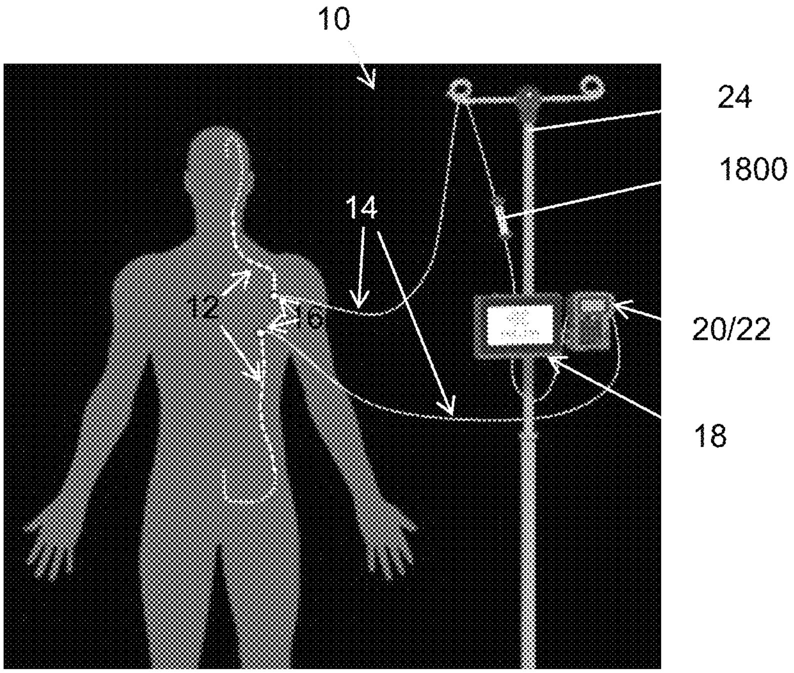
*Figure 1A: CSF Circuit*
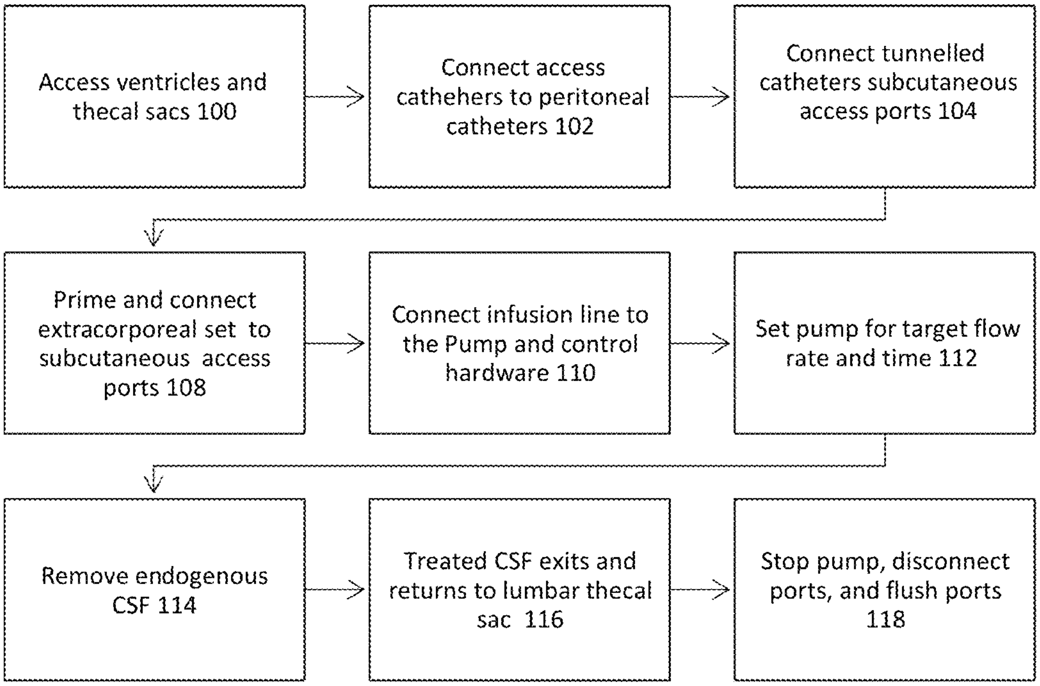
*Figure 1C: High-level surgical flow*

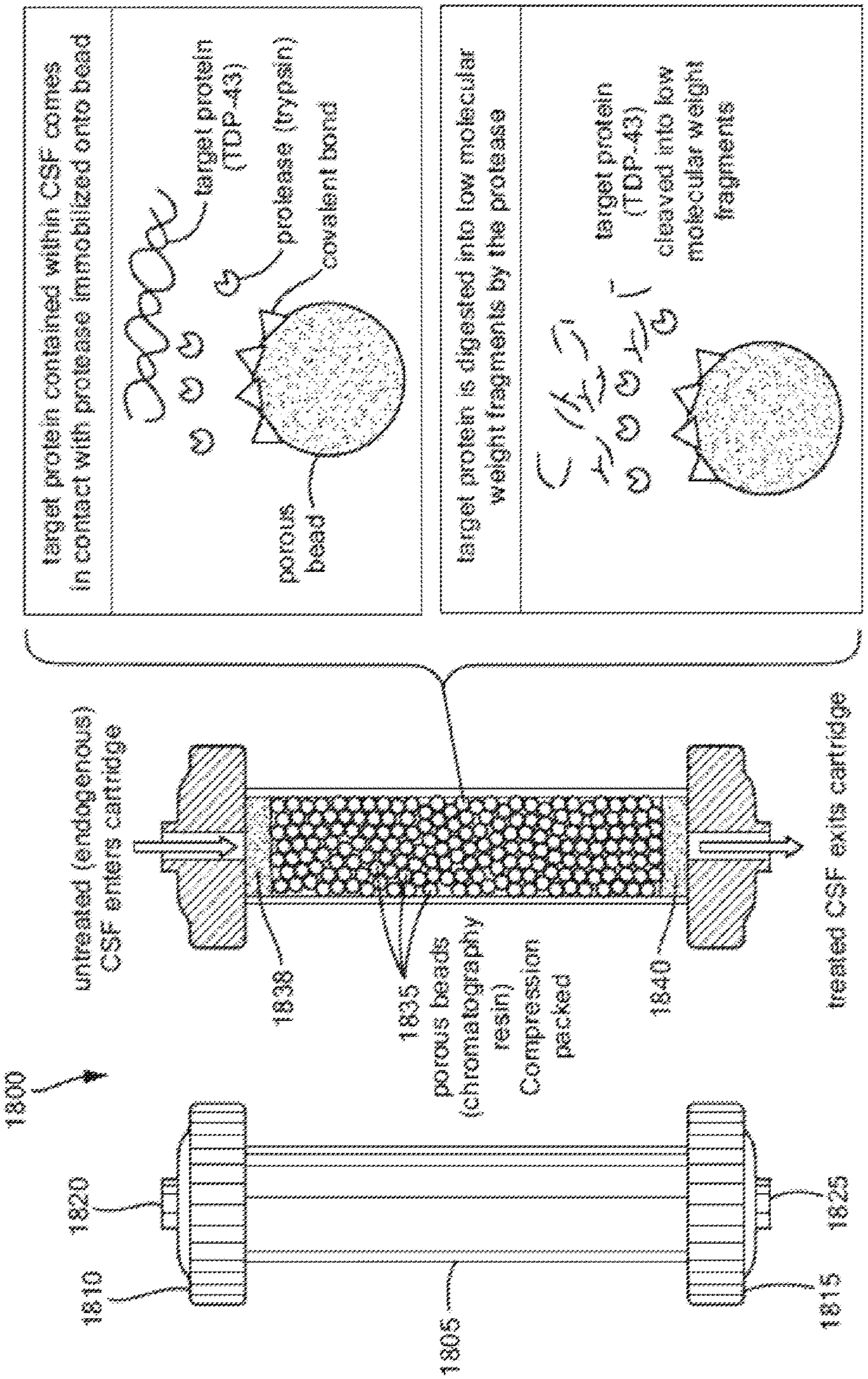
Figure 2: cartridge

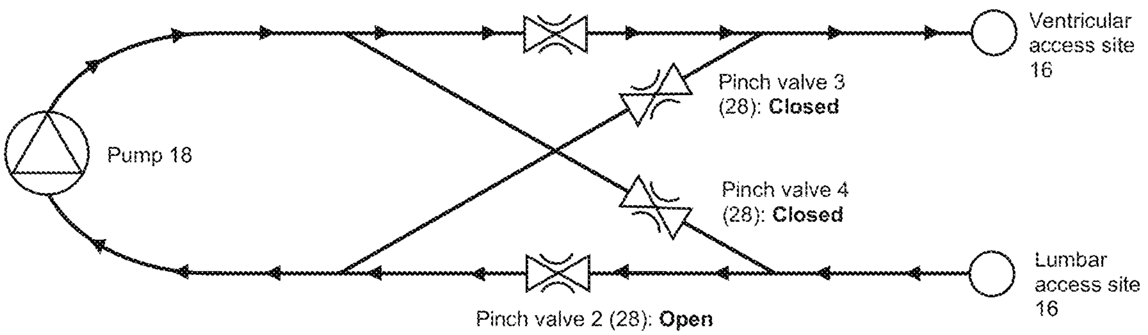
*Figure 7: Directing flow from lumbar to ventricle*
To direct flow from ventricle to lumbar:
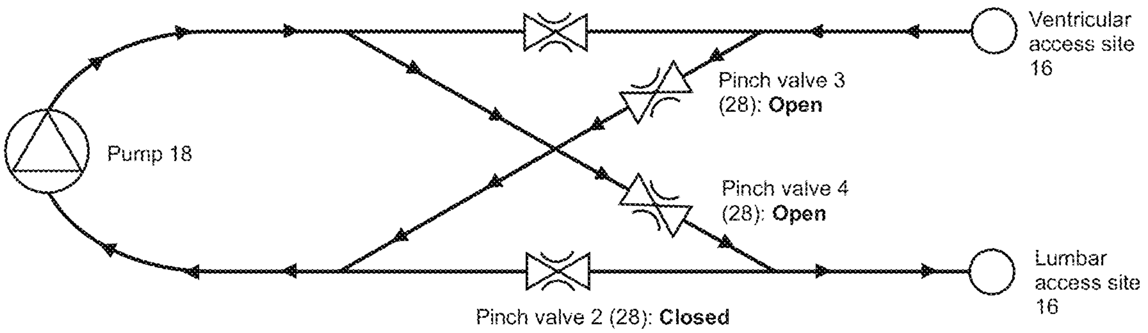
*Figure 8: Directing flow from ventricle to lumbar*

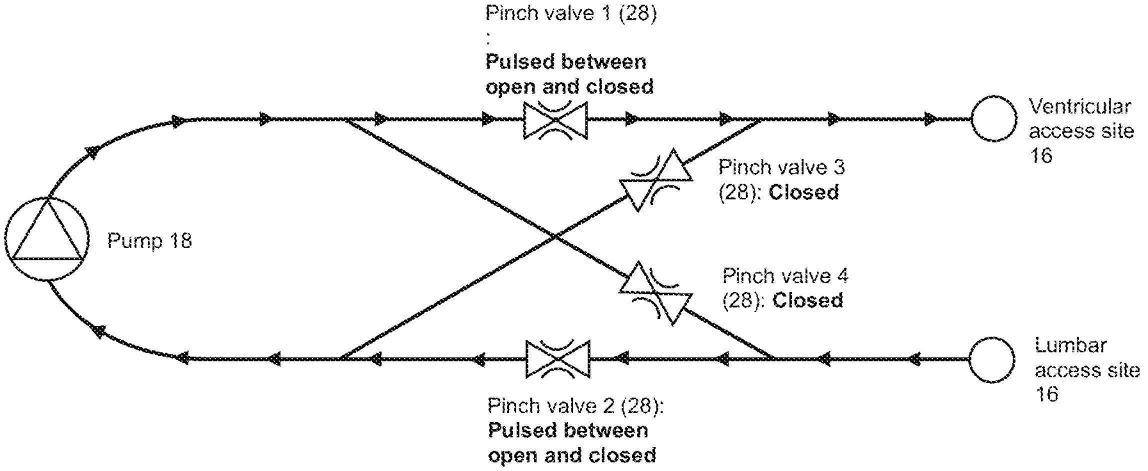
*Figure 9: Flowing from lumbar to ventricle with a pulsatile flow pattern*
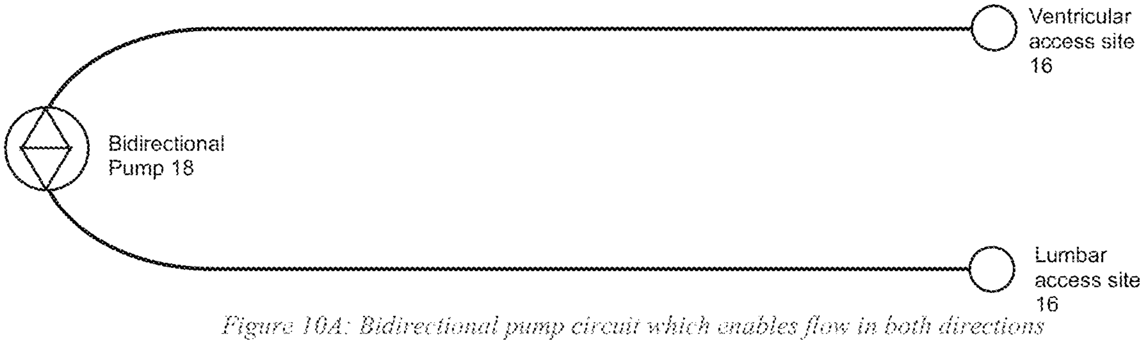
*Figure 10A: Bidirectional pump circuit which enables flow in both directions*

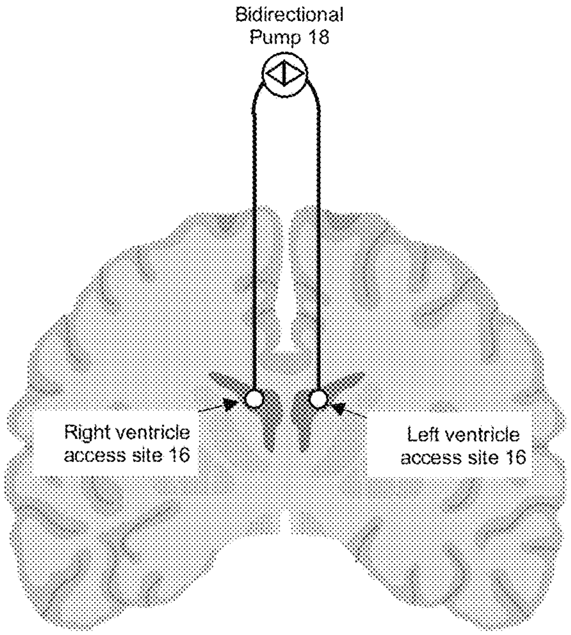
*Figure 10B: Bidirectional pump circuit which enables flow in both directions between right and left ventricles in the brain*
20/22
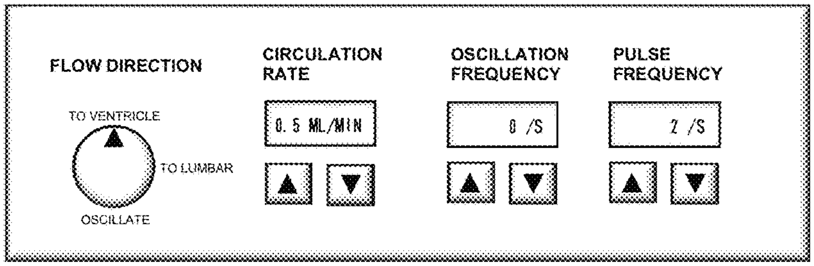
*Figure 11: System interface with controls for flow direction of CSF, circulation rate, frequency of oscillations between flow directions, and pulse frequency*

SYSTEM AND METHOD FOR CONTROLLING CSF FLOW AND MANAGING INTRACRANIAL PRESSURE

PRIORITY

This patent application claims priority from Provisional U.S. Patent Application No. 63/088,401, filed Oct. 6, 2020, entitled, "SYSTEMS, DEVICES, AND METHODS OF FLUID MANAGEMENT AND DRUG DELIVERY," and naming Gianna N. Riccardi, William X Siopes, Marcie Glicksman, Anthony DePasqua, and Kevin Kalish as inventors, the disclosure of which is incorporated herein, in its entirety, by reference.

RELATED APPLICATIONS

This patent application is related to the following patent applications filed on Sep. 29, 2021 with the same applicant and some overlapping inventors. All three of these patent applications are incorporated herein, in their entireties, by reference.

U.S. application Ser. No. 17/489,620,
U.S. application Ser. No. 17/489,625, and
U.S. application Ser. No. 17/489,633.

GOVERNMENT RIGHTS

None

FIELD

Illustrative embodiments generally relate to medical devices and methods and, more particularly, illustrative embodiments relate to devices and methods for managing subarachnoid fluid, such as cerebrospinal fluid ("CSF"), and/or drug delivery that may be used to treat neurodegenerative disorders.

BACKGROUND

Intrathecal drug delivery via the cerebrospinal fluid presents a number of safety issues. In particular, it can present significant risk to a patient if it overly increases or overly decreases the intracranial pressures.

SUMMARY OF VARIOUS EMBODIMENTS

In accordance with one embodiment of the invention, a CSF management method and/or apparatus is used with a patient forms a CSF circuit having at least one pump and catheter. The CSF circuit is configured to control the flow of CSF in the patient's body. The method then flows, using the pump and the catheter, the patient's CSF at a given flow rate through the CSF circuit, and monitors, using a pressure sensor, the intracranial pressure in the craniospinal compartment of the patient when flowing CSF through the CSF circuit. For safety purposes, the method controls the given flow rate of the CSF in the CSF circuit as a function of the monitored intracranial pressure in the craniospinal compartment.

The method may set a high threshold pressure value and/or a low threshold value. When setting a high threshold value, the method/apparatus may reduce the given flow rate of the CSF when the intracranial pressure is detected to be equal to or greater than the high threshold pressure value. In a corresponding manner, when setting a low threshold value, the method/apparatus may reduce the given flow rate of the CSF when the intracranial pressure is detected to be equal to or greater than the high threshold pressure value. To alert a caregiver, the method/apparatus may produce an alert when the intracranial pressure is equal to or greater than a high threshold pressure value or when the intracranial pressure is equal to or less than a low threshold pressure value. To keep the caregiver apprised, the method/apparatus may produce output information for use by a display to display indicia indicating information relating to the intracranial pressure The method/apparatus may receive a pressure threshold range (e.g., 5-25 mm Hg, or 10-20 mm Hg). That pressure threshold range may have a difference between its high threshold pressure value and low threshold pressure value of between 10 and 20 mm Hg. In that case, the method/apparatus may control the given rate by maintaining the given flow rate a prescribed value when the intracranial pressure is within the pressure threshold range. However, the method/apparatus may modify the given flow rate to a different value when the intracranial pressure is detected to be outside of the pressure threshold range.

The CSF circuit preferably is a closed fluid circuit. For example, the CSF circuit may include a fluid port into the patient. In that case, the catheter may be removably coupled with the port. Among other locations, the CSF circuit may access one or more CSF-containing compartments within patient anatomy, including one or more of the lateral ventricles, the lumbar thecal sac, the third ventricle, the fourth ventricle, and the cisterna magna.

Some embodiments may flow the CSF may maintaining the given flow rate at a substantially constant rate when the intracranial pressure is between a high threshold pressure value and a low threshold pressure value. Moreover, to treat the CSF, the CSF circuit may have a port for removably coupling configured to removably couple with a cartridge configured to mix CSF with a material (e.g., a drug, therapeutic, or similar) to produce a mixed CSF/material. The cartridge has an output to move the mixed CSF/material from of the cartridge and into the catheter.

A number of different implementations may use various pressure sensors in the CSF circuit. For example, the CSF circuit may use a load cell. Accordingly, the method/apparatus may monitor by receiving a pressure signal from the load cell. Among other things, the pressure signal may have information relating to the intracranial pressure.

In accordance with another embodiment, a CSF management system has a CSF circuit that includes a catheter and a valve. The CSF circuit is configured to coordinate with at least one pump, controls flow of the patient's CSF, and is removably couplable with the patient's port. The system also has a pressure sensor operably couplable with the catheter. The pressure sensor is configured to monitor the intracranial pressure in the craniospinal compartment of the patient when flowing CSF through the CSF circuit. A controller is configured to control the pump to flow the CSF at a given flow rate through the CSF circuit. The controller also is configured to control the given flow rate of the CSF in the CSF circuit as a function of the monitored intracranial pressure in the craniospinal compartment.

Illustrative embodiments of the invention are implemented as a computer program product having a computer usable medium with computer readable program code thereon. The computer readable code may be read and utilized by a computer system in accordance with conventional processes.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

FIG. 1A schematically shows a cerebrospinal fluid circuit that may be used with illustrative embodiments of the invention.

FIG. 1C shows a high level surgical flow process in accordance with illustrative embodiments.

FIG. 2 shows a schematic of a cartridge, in accordance with some embodiments of the present disclosure.

FIG. 7 schematically shows directing flow from lumbar to ventricle in accordance with illustrative embodiments.

FIG. 8 schematically shows directing flow from ventricle to lumbar in accordance with illustrative embodiments.

FIG. 9 schematically shows directing flow from lumbar to ventricle with a pulsatile pattern in accordance with illustrative embodiments.

FIGS. 10A and 10B schematically show bidirectional pump circuits that enable flow in two opposite directions (FIG. 10B between right and left ventricles in the brain) in accordance with illustrative embodiments.

FIG. 11 schematically shows another system interface in accordance with illustrative embodiments.

DESCRIPTION OF ILLUSTRATIVE EMBODIMENTS

Figure 1B:
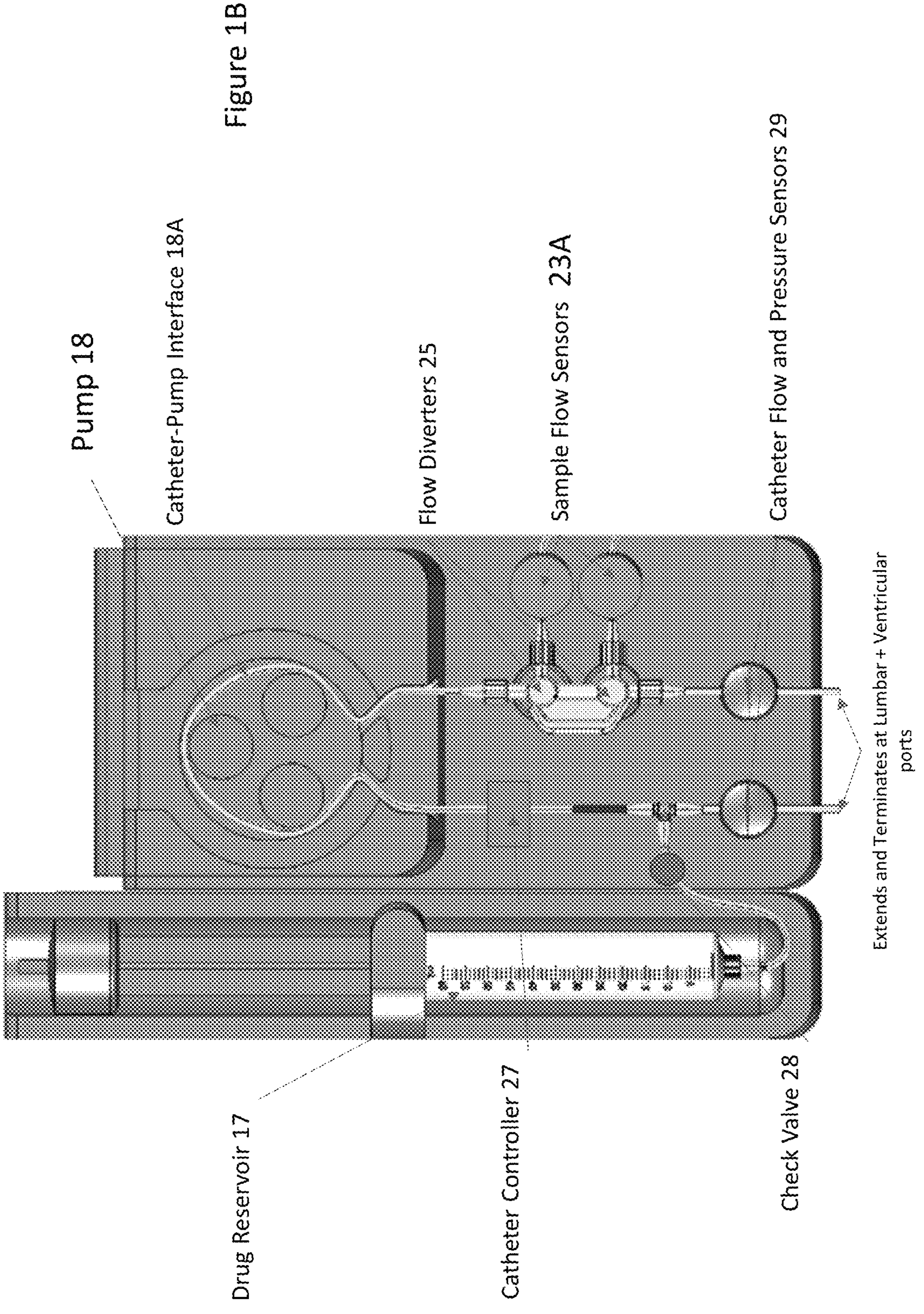
FIG. 1B schematically shows an external catheter configured in accordance with illustrative embodiments.

Illustrative embodiments manage the flow of cerebrospinal fluid ("CSF") in a mammalian body to minimize the risks associated with unregulated or extreme intracranial pressures. To that end, a CSF management system, either directly or indirectly, controls CSF flow through its CSF circuit when such pressures extend beyond a prescribed pressure range. The system thus includes a flow controller that controls various functional components in the CSF circuit, such as one or more pumps, valves, and/or catheters/tubing, to control the CSF flow rate as a function of measured or otherwise determined intracranial pressures.

The CSF circuit also optionally can include a reloadable cartridge that can quickly connect and detach to the remainder of the system without having to take apart various system components. The cartridge can include one or more valves that can regulate flow through catheters/tubing in the CSF circuit, as well as an air vent to expel and prevent excess air from entering the system. The system can be configured to send an alert to raise a warning of an intracranial issue. Moreover, the system can have a flow controller to actively monitor relevant pressure(s) and automatically adjust the flow rate in order to maintain CSF flow at a preferred rate and prevent an occlusion or significant flow reduction.

Details of illustrative embodiments are discussed below. It should be noted that this disclosure describes certain exemplary embodiments to provide an overall understanding of the principles of the structure, function, manufacture, and use of the systems, devices, and methods disclosed herein. One or more examples of these embodiments are illustrated in the accompanying drawings. Those skilled in the art will understand that the systems, compositions, and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

Many neurodegenerative diseases have been tied to the accumulation of biomolecules (e.g., toxic proteins) contained in cerebrospinal fluid (CSF) or other fluids (e.g., interstitial fluid) within the subarachnoid space (SAS) of a mammalian subject. Problematically, these (e.g., toxic) biomolecules may be secreted and then transported by the CSF to other cells in the body, which process may occur over the span of years. For example, dipeptide repeat proteins (DPRs) and/or TDP-43 have been implicated in neuronal death in the pathology of amyotrophic lateral sclerosis (ALS, or Lou Gehrig's disease), Alzheimer disease (AD), frontotemporal degeneration (FTD), Parkinson's disease (PD), Huntington's disease (HD), and progressive supranuclear palsy (PSP), to name just a few. Hence, research has focused primarily on the removal of harmful DPRs. Techniques for removing DPRs and/or TDP-43 have included: shunting CSF from the CSF space, diluting the CSF (e.g., with an artificial fluid), administering a drug into the CSF, conditioning the CSF, and/or manipulating CSF flow.

Recent breakthrough techniques for handling this problem include ameliorating the CSF, and treating a neurological disorder by removing or degrading a specific (toxic) protein.

Amelioration, as used in various embodiments, involves systems and methods for ameliorating a fluid in the subarachnoid space (SAS) (e.g., a cerebrospinal fluid (CSF), an interstitial fluid (ISF), blood, and the like) of a mammalian subject, unless otherwise particularly distinguished (e.g., referred to as solely CSF). Representative systems may be completely or partially implanted within the body of the mammalian subject (discussed below). Within the body, the systems and/or components thereof may also be completely or partially implanted within the SAS and exposed to the exterior via a port 16 (e.g., a medical valve that provides selective access to the interior system components). These systems execute processes that may occur entirely in-vivo, or some steps that occur extracorporeally. Illustrative embodiments ameliorate with a CSF circuit, discussed below.

Amelioration, for the purpose of illustration, may include changing the physical parameters of the fluid, as well as digestion, removal, immobilization, reduction, and/or alteration, to become more acceptable and/or inactivation of certain entities, including: target molecules, proteins, agglomerations, viruses, bacteria, cells, couples, enzymes, antibodies, substances, and/or any combination thereof. For example, in some embodiments and applications, amelioration may refer to removing toxic proteins from or conditioning one or more of the blood, interstitial fluid, or glymph contained therein, or other fluid, as well as the impact that this removal has on treating diseases or conditions that affect various bodily functions, (i.e., improving the clinical condition of the patient). Moreover, amelioration may be performed by any one of: digestion, enzymatic digestion, filtration, size filtration, tangential flow filtering, countercurrent cascade ultrafiltration, centrifugation, separation, magnetic separation (including with nanoparticles and the like), electrophysical separation (performed by means of one or more of enzymes, antibodies, nanobodies, molecular imprinted polymers, ligand-receptor complexes, and other charge and/or bioaffinity interactions), photonic methods (including fluorescence-activated cell sorting (FACS), ultraviolet (UV) sterilization, and/or optical tweezers), photoacoustical interactions, chemical treatments, thermal methods, and combinations thereof. Advantageously, various embodiments or implementations of the present invention may reduce levels of toxicity and, after reduced, facilitate maintaining the reduced levels over time.

The extent of amelioration, as reflected by the concentration of the target biomolecules, may be detected through a variety of means. These include optical techniques (e.g., Raman, coherent Stokes, and anti-Stokes Raman spectroscopy; surface enhanced Raman spectroscopy; diamond nitrogen vacancy magnetometry; fluorescence correlation spectroscopy; dynamic light scattering; and the like) and use of nanostructures such as carbon nanotubes, enzyme linked immunosorbent assays, surface plasmon resonance, liquid chromatography, mass spectrometry, circular proximity ligation assays, and the like.

Amelioration may include the use of a treatment system (e.g., UV radiation, IR radiation), as well as a substance, whose properties make it suitable for amelioration. Amelioration of CSF or ameliorated CSF—which terms may be used interchangeably herein—refers to a treated volume of CSF in which one or more target compounds have been partially, mostly, or entirely removed. It will be appreciated that the term removed, as used herein, can refer not only to spatially separating, as in taking away, but also effectively removing by sequestering, immobilizing, or transforming the molecule (e.g., by shape change, denaturing, digestion, isomerization, or post-translational modification) to make it less toxic, non-toxic or irrelevant.

The term, "ameliorating agent" generally refers to a material or process capable of ameliorating a fluid, including enzymes, antibodies, or antibody fragments, nucleic acids, receptors, anti-bacterial, anti-viral, anti-DNA/RNA, protein/amino acid, carbohydrate, enzymes, isomerases, compounds with high-low biospecific binding affinity, aptamers, exosomes, ultraviolet light, temperature change, electric field, molecular imprinted polymers, living cells, and the like. Additional details of amelioration are taught by the incorporated related applications, as well as in PCT Application No. PCT/US20/27683, filed on Apr. 10, 2020, the disclosure of which is incorporated herein, in its entirety, by reference. In a similar manner, details for further treatments are taught by PCT Application No. PCT/US19/042880, filed Jul. 22, 2019, the disclosure of which is incorporated herein, in its entirety, by reference.

To control CSF flow within the body (e.g., through the ventricle), illustrative embodiments form a CSF circuit/channel (identified by reference number "10") that manages fluid flow in a closed loop. FIG. 1A, for example, shows one embodiment of such a CSF circuit 10. In this example, internal catheters 12 (also referred to generically as "tubing" or the like) positioned in-vivo/interior to the body fluidly couple together via the subarachnoid space. To that end, a first internal catheter 12 fluidly couples a prescribed region of the brain (e.g., the ventricle) to a first port 16, which itself is configured and positioned to be accessible by external components. In a corresponding manner, a second catheter couples the lumbar region or the lower abdomen of the subarachnoid space with a second port 16 that, like the first port 16, also is configured to be positioned and accessible by external components.

The first and second ports 16 may be those conventionally used for such purposes, such as a valved Luer-lock or removable needle. The first and second internal catheters 12 thus may be considered to form a fluid channel extending from the first port 16, to the ventricle, down the spine/subarachnoid space to the lumbar, and then to the second port 16. These internal components, which may be referred to as "internal CSF circuit components," are typically surgically implanted by skilled professionals in a hospital setting.

The CSF circuit 10 also has external components (referred to as "external CSF circuit components). To that end, the external CSF circuit components include at least two fluid conduits 14. Specifically, the external CSF circuit components include a first external fluid conduit 14, that couples with the first port 16 for access to the ventricle. The other end of the first external conduit 14 is coupled with a management system 19, which includes one or more CSF pumps (all pumps are generically identified in the figures as reference number "18"), one or more user interface/displays 20, one or more drug pumps 18, and a control system/controller 22. The fluid external fluid conduit 14 may be implemented as a catheter and thus, that term may be used interchangeably with the term "conduit" and be identified by the same reference number 14.

Illustratively, this management system 19 is supported by a conventional support structure (e.g., a hospital pole 24 in FIG. 1A). To close the CSF circuit 10, a second external catheter 14 extends from that same CSF management system 19 and couples with the second port 16 and the management system 19. This management system 19 and external catheters 14 therefore form the exterior part of a closed CSF circuit 10 for circulating the CSF and therapeutic material.

It should be noted that the CSF circuit 10 may have one or more components between the first and second ports 16 and the respective removable connections of the first and second external catheters 14. For example, the first port 16 may have an adapter that couples with the first external catheter 14, or another catheter with a flow sensor may couple between such external catheter 14 and port 16. As such, this still may be considered a removable connection, albeit an indirect fluid connection. There may be corresponding arrangements with the other end of the first external catheter 14, as well as corresponding ends of the second external catheter 14. Accordingly, the connection can be a direct connection or an indirect connection.

The first and second external catheters 12 and 14 preferably are configured to have removable connections/couplings with the management system 19, as well as their respective ports 16. Examples of removable couplings may include a screw-on fit, an interference fit, a snap-fit, or other known removable couplings known in the art. Accordingly, a removable coupling or removable connection does not necessarily require that one forcibly break, cut, or otherwise permanently break the ports 16 for such a connection or disconnection. Some embodiments, however, may enable a disconnection form the first and/or second ports 16 via breaking or otherwise, but the first and/or second ports 16 should remain in-tact to receive another external catheter 14 (e.g., at the end of life of the removed external catheter 14).

FIG. 1B schematically shows more details of the first and/or second external conduits/catheters 14. This figure shows an example of an external catheter 14 operating with other parts of the system. As shown, in this example, the system receives an optional drug reservoir 17 (e.g., a single-use syringe) configured to deliver a dose of therapeutic material (e.g., a drug) that fluidly couples with the catheter 14 via a check valve 28 and T-port on the catheter 14. In addition, the catheter 14 is coupled with a mechanical pump 18 and also preferably includes a sample port 23 with flow diverters 25 for diverting flow toward or away from a sample port 23. The sample port 23 preferably has sample port flow sensors 23A to track samples.

Some embodiments may be implemented as a simple catheter having a body forming a fluid-flow bore with removably couplable ends (or only one removably couplable end). Illustrative embodiments, however, add intelligence to make one or both of these external catheters 14 "smart" catheters, effectively creating a more intelligent flow system. For example, either one or both of the external catheters 14 can have a processor, ASIC, memory, EEPROM (discussed below), FPGAs, RFID, NFC, or other logic (generally identified as reference number "27") configured to collect, manage, control the device, and store information for the purposes of security, patient monitoring, catheter usage, or communicating with the management system 19 to actively control fluid dynamics of the CSF circuit 10. Among other things, the management system 19 may be configured to coordinate with an EEPROM 27 to control CSF fluid flow as a function of the therapeutic material infusion flow added to the CSF circuit 10 (discussed below) via the check valve 28 at the output of the drug reservoir 17.

As shown in FIG. 1B, one embodiment of the external catheter 14 has electrically erasable programmable read-only memory, EEPROM 27, (or other logic/electronics) that can be implemented to accomplish a variety of functions. Among others, the EEPROM 27 can ensure that the CSF circuit 10 and its operation is customized/individualized to a patient, a treatment type, a specific disease, and/or a therapeutic material. For example, in response to reading information stored in the EEPROM 27, the control system 22 may be configured to control fluid flow as a function of the therapeutic material.

Importantly, as a disposable device, the EEPROM 27 or other logic of the external catheter 14 can be configured to provide alerts, and/or produce or cause production of some indicia (e.g., a message, visual indication, audio indication, etc.) indicating that the external catheter 14 has reached an end of its lifecycle, or indicating how much of its lifecycle remains. For example, an external surface of the catheter 14 may have a tag that turns red when the EEPROM 27 and/or other logic 27 determines that the external catheter 14 has reached its full lifetime use. For example, the external catheter 14 may be considered to have a usage meter, implemented as some logic or EEPROM 27, configured to track use of the CSF fluid conduit 14 to help ensure it is not used beyond its rated lifetime. Moreover, the logic or EEPROM 27 can register with the control system 22 to start use timers to reduce tampering or use beyond a lifetime.

Some embodiments have a printable circuit board (PCB) equipped with a wireless interface (e.g., Bluetooth antenna) or a hardware connection configured to communicate the pump 18 and/or control system 22. The external catheter 14 can be configured to time out after a certain period, capture data, and communicate back and forth with the control system 22 or other off-catheter or on-catheter apparatus to share system specifications and parameters. The intelligent flow catheter 14 can be designed with proprietary connections such that design of knockoffs or cartridges 26 (discussed below) can be prevented to ensure safety and efficacy of the CSF circuit 10 and accompanying processes.

In addition to the management logic, the external catheter(s) 14 also may have a set of one or more flow sensors and/or a set of one or more pressure sensors. Both of those flow sensors are shown generically at reference number 29, and may be located upstream or downstream from their locations in FIG. 1B. For example, the left sensor(s) 29 generically shown in FIG. 1B can be a flow sensor, pressure, or both a flow sensor and pressure. The same can be said for the right sensor(s) 29 generically shown in FIG. 1B. They preferably are positioned between the ports 16 on the body and the remaining components as shown.

Of course, the flow sensor(s) 29 may be configured to detect flow through the bore of the catheter body, while the pressure sensor(s) 29 may be configured to detect pressure within the bore of the body. Among other functions, the flow sensor(s) 29 may monitor flow rate of fluid through the conduit bore and/or total flow volume through the conduit bore.

The catheter 14 preferably is configured to have different hardness values at different locations. Specifically, illustrative embodiments may use a mechanical pump 18, as shown and noted above. The pump 18 may periodically urge a compressive force along that portion of the catheter 14 it contacts at its interface 18A with the catheter 14. The outlet of the pump 18 in this case may be the portion of the catheter 14 that is receiving the output of a neighboring compressed catheter portion (e.g., a portion that is adjacent to the compressed catheter portion(s). To operate efficiently, illustrative embodiments form the catheter 14 to have a specially configured hardness at that location (e.g., 25-35 Shore A). Diameter also is important for flow and thus, one skilled in the art should determine appropriate diameters as a function of performance and durometer/hardness. Preferably, the catheter portion that contacts the pump 18 is softer than the remainder of the catheter 14, although both could have the same hardness. Accordingly, the catheter preferably has a variable hardness along its length and may even have a variable diameter.

Alternative embodiments may provide an open-loop CSF fluid circuit 10. For example, the CSF fluid circuit 10 may have an open bath (not shown) to which fluid is added and then removed. The inventors expect the closed-loop embodiment to deliver better results, however, than those of the open-loop CSF fluid circuit 10.

Illustrative embodiments are distributed to healthcare facilities and/or hospitals as one or more kits. For example, one more inclusive kit may include the internal and external catheters 12 and 14. Another exemplary kit may include just the internal catheters 12 and the ports 16 (e.g., for a hospital), while a second kit may have the external catheters 14 and/or a single-use syringe. Other exemplary kits may include the external catheters 14 and other components, such as the management system 19 and/or a CSF treatment cartridge 1800. See below for various embodiments of the CSF circuit 10 and exterior components that also may be part of this kit.

Accordingly, when coupled, these pumps 18, valves (discussed below and all valves generally identified by reference number 28), internal and external catheters 14, and other components may be considered to form a fluid conduit/channel that directs CSF to the desired locations in the body in a prescribed or controlled manner. It should be noted that although specific locations and CSF containing compartments are discussed, those skilled in the art should recognize that other compartments can be managed (e.g., the lateral ventricles, the lumbar thecal sac, the third ventricle, the fourth ventricle, and/or the cisterna magna). Rather than accessing the ventricle and the lumbar thecal sac, both lateral ventricles could be accessed with the kit. With both internal catheters 12 implanted, CSF may be circulated between the two lateral ventricles, or a drug could be delivered to both ventricles simultaneously.

FIG. 1C shows a high level surgical flow process that may incorporate the CSF circuit 10 of FIG. 1A in accordance with illustrative embodiments of the invention. It should be noted that this process is substantially simplified from a longer process that normally would be used to complete the surgical flow. Accordingly, this process may have many additional steps that those skilled in the art likely would use. In addition, some of the steps may be performed in a different order than that shown, or at the same time. Those skilled in the art therefore can modify the process as appropriate. Moreover, as noted above and below, many of the materials, devices, and structures noted are but one of a wide variety of different materials and structures that may be used. Those skilled in the art can select the appropriate materials and structures depending upon the application and other constraints. Accordingly, discussion of specific materials, devices, and structures is not intended to limit all embodiments.

The process begins at step 100 by setting up the internal catheters 12 inside the patient. To that end, step 100 accesses the ventricles and thecal sacs using standard catheters and techniques, thus providing access to the CSF. Step 102 then connects access catheters 12 to peritoneal catheters 12, which are tunneled subcutaneously to the lower abdomen. The tunneled catheters 12 then are connected at step 104 to the ports 16 implanted in the abdomen.

At this point, the process sets up an extracorporeal circulation set (i.e., the external catheters 14, or the "smart catheters" in some embodiments). To that end, step 106 may prime and connect the extracorporeal circulation set 14 to the subcutaneous access ports 16. Preferably, this step uses an extracorporeal circulation set, such as one provided by Endear Therapies, Inc. of Newburyport, MA, and/or the external catheters 14 discussed above. The process continues to step 110, which connects an infusion line or other external catheter 14 to the management system 19, and then sets the target flow rate and time. At this point, setup is complete and treatment may begin (step 112).

The process then removes endogenous CSF from the ventricle. This CSF may then be passed through a digestion region (e.g., through a cartridge 1800 having a specific digesting material), where certain target proteins in the CSF are digested. For example, the cartridge 1800 may have an inner plenum space 1830 of the cartridge 1800 filled with a plurality of (e.g., porous, chromatography resin) beads that have been compression packed. To prevent constituents from entering or escaping from the cartridge 1800, a filter membrane may be disposed at the first end of the cartridge 1800 and a second filter membrane may be disposed at the second end of the cartridge 1800. In some applications, the ameliorating agent may be decorated on the beads.

In some applications, the cartridge 1800 may be compression packed with a chromatography resin (e.g., agarose, epoxy methacrylate, amino resin, and the like) that has a protease covalently bonded (i.e. immobilized) to the three-dimensional resin matrix. The selected protease may be configured to degrade and/or removing target toxic biomolecules by way of proteolytic degradation. The resin may be a porous structure having a particle size commonly ranging between 75-300 micrometers and, depending on the specific grade, a pore size commonly ranging between 300-1800 Å. Thus, at a high level, the cartridge 1800 has ameliorating agent that removes and/or substantially mitigates the presence of toxic proteins from the CSF.

This and similar embodiments may consider this to be an input for the digesting enzyme. Any location providing access to the drug may be considered to be an input for the drug. At step 116, the treated CSF exits the digestion region and is returned via the CSF circuit 10 to the lumbar thecal sac. The process concludes at step 118, which stops the pump 18 when treatment is complete. The management system 19 then may be disconnected and the ports 16 flushed.

Cartridge Details in Illustrative Embodiments

FIG. 2 shows one embodiment of the above noted cartridge 1800. In some embodiments, the cartridge 1800 can include a commercially-available chromatography column 1805 such as the OPUS® MiniChrom (11.3 mm×5 mL, REP-001) manufactured by Repligen Corporation of Waltham, Massachusetts. The cartridge 1800 may have a first end to which a first cap 1810 is removably attachable (e.g., by friction fit, screw on, snap on, and so forth), as well as a second end to which a second cap 1815 is removably attachable (e.g., by friction fit, screw on, snap on, and so forth). Each of the caps 1810, 1815 may include an opening through which a first (e.g., upstream) conduit 1820 or a second (e.g., downstream) conduit 1825 may be inserted to provide fluidic communication to and through the cartridge 1800. In some embodiments, the inner plenum space 1830 of the cartridge 1800 may be filled with a plurality of (e.g., porous, chromatography resin) beads 1835 that have been compression packed. To prevent constituents from entering or escaping from the cartridge 1800, a first filter membrane 1838 may be disposed at the first end of the cartridge 1800 and a second filter membrane 1840 may be disposed at the second end of the cartridge 1800. In some applications, the ameliorating agent has been decorated on the beads 1835.

In some applications, the cartridge 1800 may be compression packed with a chromatography resin (e.g., agarose, epoxy methacrylate, amino resin, and the like) that has a protease covalently bonded (i.e. immobilized) to the three-dimensional resin matrix. The selected protease is capable of degrading and/or removing target toxic biomolecules by way of proteolytic degradation. The resin is a porous structure having a particle size commonly ranging between 75-300 micrometers and, depending on the specific grade, a pore size commonly ranging between 300-1800 Å.

To preserve proper function and sterility of the cartridge 1800, the cartridge manufacturing process should be carefully managed. For example, the activity of the cartridge 1800 or the availability of active sites of the protease to digest target proteins and inhibition of microbial growth within the resin matrix is important. In some implementations, particle size may be about 1-50 micrometers and pore size may be about 8-12 nanometers. In some applications, a narrow distribution of pore size may be desirable, while in other applications, a broad distribution of pore size may be desirable. In still other applications, a multimodal distribution of pore size may be desirable.

In the case of cartridge activity, it is common to fill the column with a buffer solution for preservation. Buffers are intended to inhibit autocatalysis and prevent the reduction of active sites on the available surface area of the resin matrix. One example of a buffer solution that has been successfully implemented is 10 mM HCl with 20 mM CaCl2 at pH 2 and stored at 4° C., though it will be appreciated that, in some embodiments, the temperature can range from 2-8° C. In some variations, buffers may include: PBS 1× may be used as an immobilization buffer, Ethanolamine 1M, pH 7.5 may be used as a blocking buffer, PBS 1×/0.05% ProClin 300 may be used as a storage buffer, and HBSS may be used as a digestion buffer.

In the case of inhibiting microbial growth, it is common to assemble similar components in an environment that is either clean (e.g., in compliance with ISO 14644-1 Cleanroom Standards) or sterile in order to avoid the introduction of microorganisms, followed by a sterilization process utilizing proven approaches such as gamma irradiation, x-ray, UV, electron beam, ethylene oxide, steam, or combinations thereof.

Another variable that may be controlled to inhibit the growth of microorganisms and/or to influence the inhibition of autodegradation of enzymes is the pH level of the solution. Solutions with a pH of 2 may be successfully implemented; however, solutions with a pH in the range of about 3 to about 7.5 pH are possible.

Yet another variable that can be controlled to inhibit the growth of microorganisms is temperature. Chromatography columns are commonly stored at temperatures in the range of 2-8° C., which range has been proven to be effective and widely accepted. Storage may be kept within this temperature range until the cartridge 1800 is ready to use.

Manufacture of the cartridge 1800 may occur in a near-ambient temperature cleanroom (e.g., ISO Class 8) environment. In illustrative embodiments, this manufacturing process includes packing the resin (with immobilized enzyme) onto the chromatography column 1805 and packaging in a double-layer film polypropylene package. The packaged cartridge 1800 may then be prepared for the sterilization process, which may be gamma sterilization. Gamma sterilization has been identified as the exemplary sterilization technique, which is primarily driven by the presence of a liquid buffer. Techniques such as ethylene oxide and steam may be unlikely to penetrate and permeate the liquid adequately to achieve the necessary level of sterility. Ideally, the cartridge 1800 should be refrigerated as soon as it is produced and kept refrigerated during transport to and from the sterilization. After the cartridge 1800 completes the sterilization process, it can be shipped (e.g., after refrigeration) to a final destination, such as a contract manufacturer or inventory holding area, where it can be stored at 2-8° C.

In use, the cartridge 1800 may be retrieved from its temperature-controlled environment and staged at the point-of-care (POC). At the POC, the cartridge 1800 may be removed from its sterile packaging and subjected to a flushing protocol to wash away the buffer solutions, as well as any potentially unwanted residual components, such as unbound enzyme. Flushing or washing mitigates the risk of residual/detached trypsin or other amelioration agent from entering the body when treated CSF is returned to the subject.

The flushing protocol may require a plurality of flushing procedures using various volumes of a flushing solution. Advantageously, the flushing protocol may ensure that any potential residual amelioration agent or enzyme (e.g., trypsin) that may elute from the cartridge 1800 is flushed out. For example, in some implementations, the cartridge 1800 may be flushed with approximately one column volume (i.e., 1.0 CV) of a solution (e.g., phosphate-buffered saline (PBS)). PBS has been shown to eliminate trace amounts of residual enzyme. A higher volume of solution could be used for added assurance. For example, the cartridge 1800 could be flushed with 5-6 CVs (or 25-30 Ml) for a 5 mL column 1805. In some variations, for more consistent flow through the porous chromatography resin, the temperature of the cartridge 1800 may be raised above ambient temperatures. An exemplary flushing protocol may include flushing with 6 CVs (or 30 mL) of PBS followed by a second flushing 6 CV or 30 mL of Hanks' Balanced Salt solution (HESS).

In one implementation, as mentioned above, the ameliorating agent modifies or degrades the biomolecule present in the CSF by enzymatic digestion and, in some variations, the enzyme used for enzymatic digestion may be a protease. A person skilled in the art will recognize that various protease and resin combinations can be used with the present embodiments to tailor the specificity of the proteolytic digestion. Some non-limiting examples of proteases can include (whether or not using the cartridge 1800 for application): trypsin; elastase; cathepsin; clostripain; calpains, including calpain-2; caspases, including caspase-1, caspase-3, caspase-6, caspase-7, and caspase-8; M24 homologue; human airway trypsin-like peptidase; proteinase K; thermolysin; Asp-N endopeptidase; chymotrypsin; LysC; LysN; glutamyl endopeptidase; staphylococcal peptidase; arg-C proteinase; proline-endopeptidase; thrombin; cathepsin E, G, S, B, K, L1; Tissue Type A; heparinase; granzymes, including granzyme A; meprin alpha; pepsin; endothiapepsin; kallikrein-6; kallikrein-5; and combinations thereof.

Figure 3A:
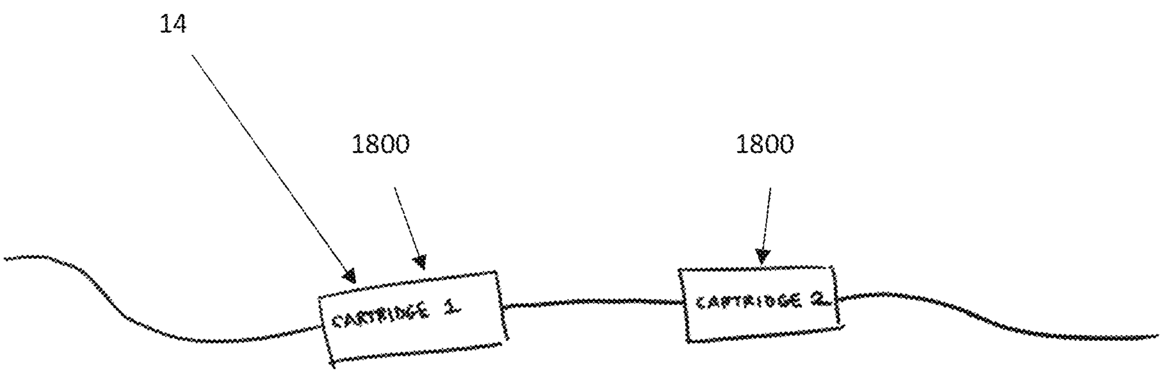
FIG. 3A shows a schematic of a plurality of cartridges connected in series in accordance with illustrative embodiments.
Figure 3B:
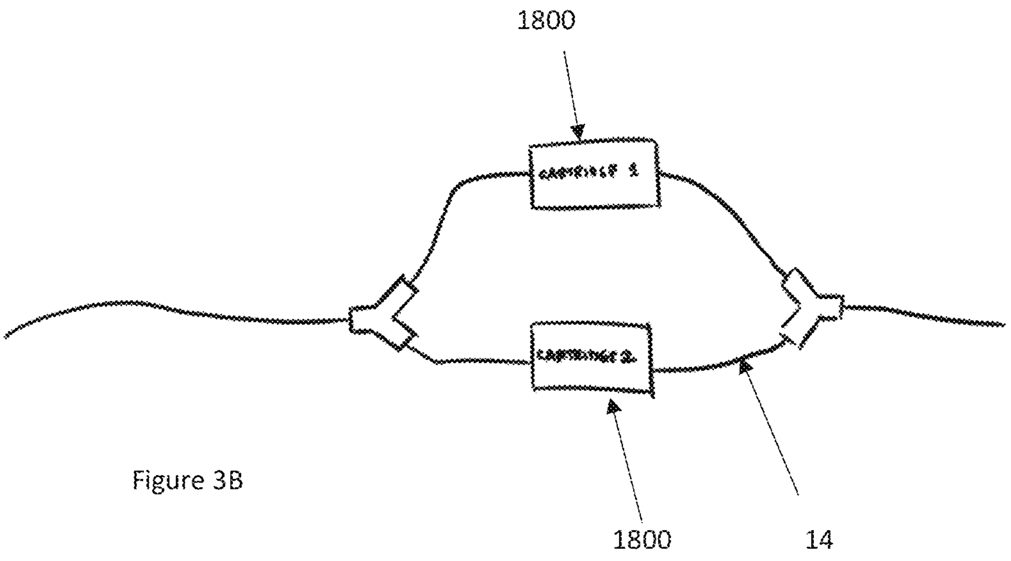
FIG. 3B shows a schematic of a plurality of cartridges connected in parallel in accordance with illustrative embodiments.

In some embodiments, a plurality of cartridges 1800 can be used to treat the CSF. The plurality of cartridges 1800 can be placed in communication with the CSF fluid path to expose the target CSF to multiple cartridges 1800. As shown, the plurality of cartridges 1800 can be positioned in series, as shown in FIG. 3A, or in parallel, as shown in FIG. 3B. Cartridges 1800 arranged in series can achieve progressive digestion of target molecules, while those arranged in parallel can digest target molecules in combination with the delivery of a therapeutic agent, as discussed further below.

Each of the plurality of cartridges 1800 can have a different protease therein, with each cartridge 1800 being targeted to degrade and/or remove one or more specific target toxic biomolecules. For example, a first cartridge 1800 can have a tailored enzyme to digest TDP-43, while a second cartridge 1800 can have a tailored enzyme that digests DPRs.

In some embodiments, the plurality of cartridges 1800 can be used for progressive digestion of specific proteins with each cartridge 1800 digesting a progressive amount of protein. That is, when arranged in series, CSF can undergo digestion in the first cartridge 1800 and flow to the second and/or subsequent cartridges 1800 where further digestion occurs such that the protein is further broken down. This progressive digestion allows for more complete removal of toxic biomolecules from the CSF to ensure that the toxic biomolecules are completely removed, or substantially completely removed from the CSF. While two cartridges 1800 are shown in the illustrative embodiments, a person skilled in the art will recognize that three or more cartridges 1800 can be used in some embodiments. These cartridges 1800 can be arranged in series, in parallel, or in a combination thereof, e.g., two cartridges 1800 in series that are in parallel with one or more additional cartridges 1800.

As discussed above, cartridges 1800 arranged in parallel can digest target molecules in combination with the delivery of a therapeutic agent. For example, in some embodiments, the first cartridge 1800 can treat and/or remove toxic biomolecules from the CSF, while the second cartridge 1800 can have a therapeutic agent therein. The therapeutic agent can decorate the beads and/or resin within the cartridge 1800 such that fluid that passes through the cartridge 1800 can be exposed to the therapeutic agent.

In some embodiments, the second cartridge 1800 can be configured to elute the therapeutic agent therefrom. For example, as the cleaned CSF leaves the first cartridge 1800, the second cartridge 1800 can elute from the second cartridge 1800 to mix with the CSF that exits the first cartridge 1800 to provide therapeutic effects to the CSF.

One or more medical Luer lock connectors or spin collars can be used by various embodiments to couple the cartridge 1800 to the CSF fluid path. For example, where standard chromatography columns are used as cartridges 1800, these medical Luer connectors can be positioned along the fluid path to attach one or more of the cartridges 1800 to the path, as shown in FIG. 3B. However, in the event that the cartridge 1800 needs replacing, this can present a complication for the clinician as they would be needed to unthread the Luer fittings and take caution to avoid spilling the patient's CSF from the line, allowing air into the line, compromising sterility, and so forth. Alternatively, the entire tube set would need to be replaced, which is undesirable.

Figure 4:
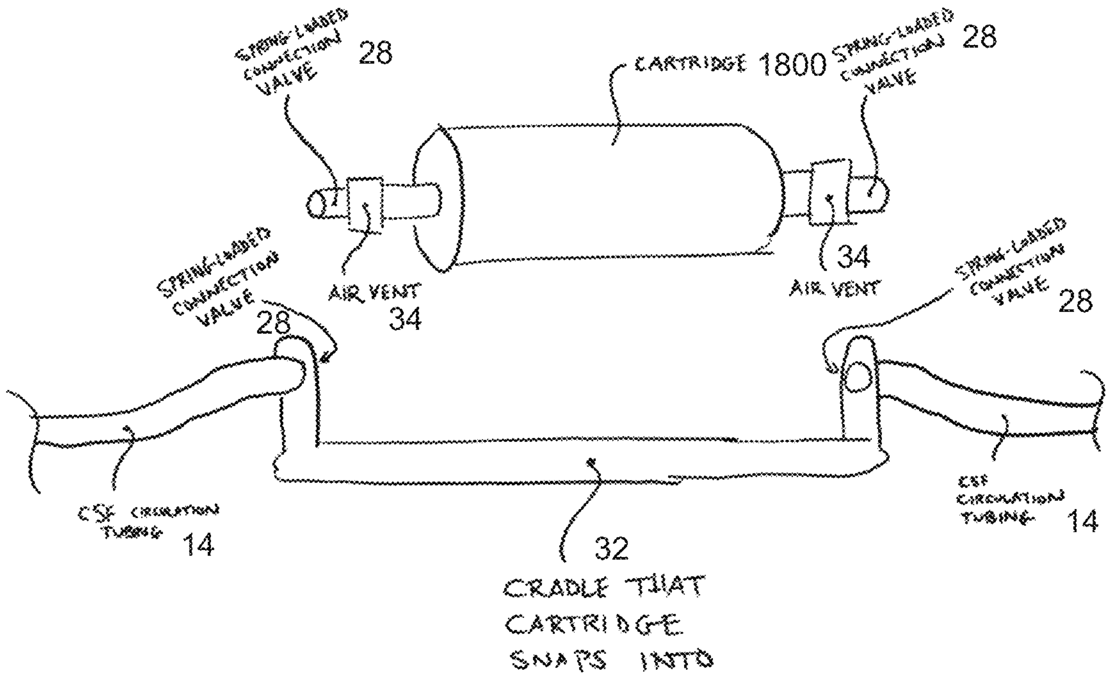
FIG. 4 schematically shows a reloadable cartridge in a CSF flow system in accordance with illustrative embodiments.

FIG. 4 illustrates an exemplary embodiment of a reloadable cartridge 1800. The reloadable cartridge 1800 can be toggled into and out of connection with the CSF circulation tubing to allow for cleaning and/or replacement of cartridges 1800. As shown, the reloadable cartridge 1800 can include one or more spring-loaded connection valves. The spring-loaded connection valves can snap into, or otherwise be received in, a cradle 32 having one or more openings to the CSF circulation tubing that allows the CSF to flow therethrough. The reloadable cartridge 1800 can include one or more air vents 34 to prevent formation of air bubbles in the CSF. Once the cartridge 1800 is no longer sufficiently active in digesting the target molecule or is clogged, the connection valves can be disconnected from the cradle 32 and the reloadable cartridge 1800 can be disconnected. It will be appreciated that the flow of CSF through the circulation tubing can be stopped and/or interrupted during cartridge 1800 replacement to ensure that the CSF does not leak out of the system 19. The system 19 can maintain sterility as there is minimal manual interaction between the user and system components. Moreover, the use of valves to stop the flow ensures little to no leaking of CSF onto system components.

In a manner similar to the external catheter(s) 14, the reloadable cartridge 1800 can have additional features added thereto to create an intelligent flow system. For example, the cartridge 1800 can have the same functionality as noted above for the external catheter(s) 14. It may have the ability to collect and store information for the purposes of security, patient monitoring, or communicating with the control system 22 (also referred to as "flow controller 22"), which is configured to control the fluid dynamics of the CSF circuit 10.

Figure 5:
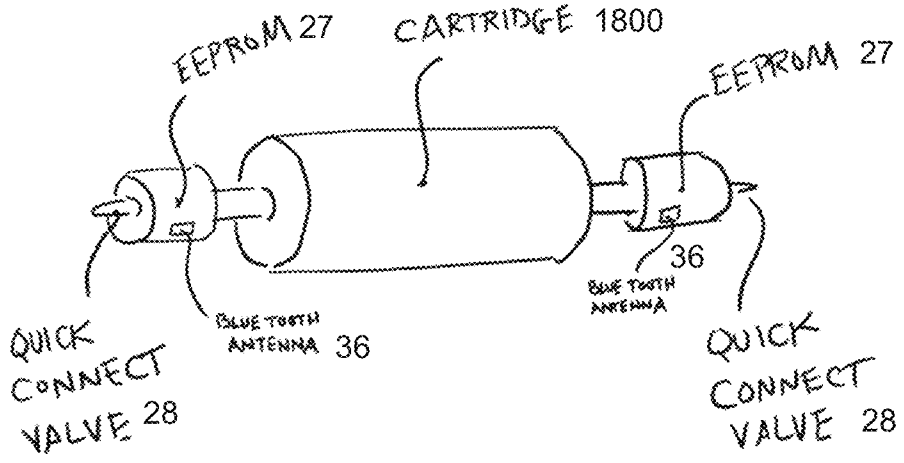
FIG. 5 schematically shows the reloadable cartridge equipped with EEPROM and/or PCB with a Bluetooth antenna in accordance with illustrative embodiments.

FIG. 5 illustrates an embodiment of a cartridge 1800 having an electrically erasable programmable read-only memory (EEPROM) that can be implemented to ensure that the system is tailored to a patient or to provide alerts that the cartridge 1800 has reached an end of its lifecycle. In some embodiments, a printable circuit board (PCB) equipped with a Bluetooth antenna 36 that is capable of communicating with a nearby controller can be used. The system 19 can be configured to time out after a certain period, capture data, and communicate back and forth with the flow controller 22 to share system specifications and parameters. The intelligent flow system can be designed with proprietary connections such that design of knockoffs or other cartridges 1800 can be prevented to ensure safety and efficacy of the system 19 and the accompanying processes.

Indeed, it should be noted that the flow controller 22 in various embodiments discussed above and below can be implemented in a variety of conventional manners, such as by using hardware, software, or a combination of hardware and software, across one or more other functional components. For example, the logic for adjusting the CSF flow rate (discussed below) may be implemented using a plurality of microprocessors executing firmware. As another example, that noted logic may be implemented using one or more application specific integrated circuits (i.e., "ASICs") and related software, or a combination of ASICs, discrete electronic components (e.g., transistors), and microprocessors. In fact, in some embodiments, certain logic in the flow controller 22 can be distributed across a plurality of different machines—not necessarily within the same housing or chassis.

Figure 6A:
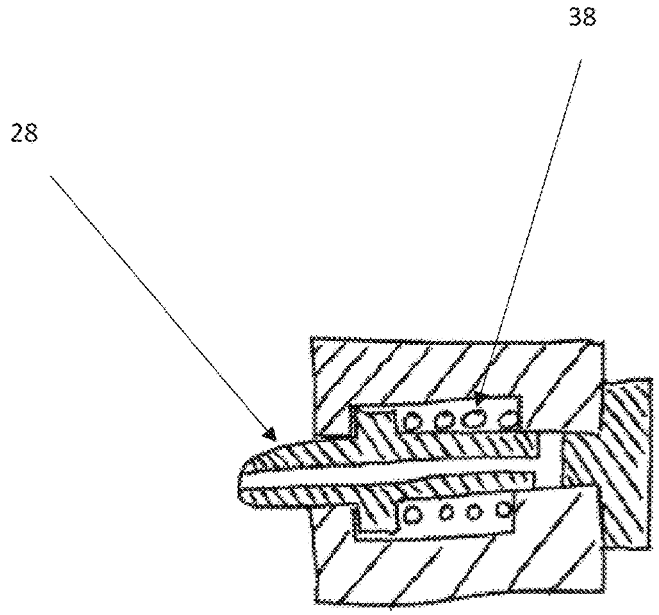
FIG. 6A schematically shows a valve of the reloadable cartridge of FIG. 4 in the closed position in accordance with illustrative embodiments.
Figure 6B:
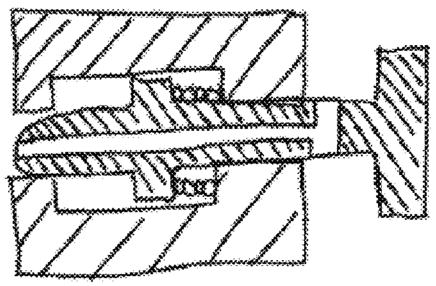
FIG. 6B schematically shows a valve of the reloadable cartridge of FIG. 4 in the open position in accordance with illustrative embodiments.

FIGS. 6A-6B illustrate an embodiment of an exemplary association between the valve of the cartridge 1800 and the CSF circulation tubing discussed above with respect to FIGS. 4 and 5. As shown, the valve 28 can be removably connected via a spring 38 (i.e., spring loaded), a plunger, and/or a poppet valve. The system can be configured to for a quick connection with the remainder of the system. As shown, FIG. 6A illustrates the valve 28 in the closed position and FIG. 6B illustrates the valve 28 in the open position as activated by the cradle 32. In the open position, when the reloadable cartridge 1800 is disposed within the cradle 32, CSF can flow through the cartridge 1800. When the cartridge 1800 is disconnected, the valve 28 can spring back to allow the plunger to abut the wall of the system to close the valve 28 and prevent the flow, and therefore minimize and/or eliminate leakage of CSF.

Monitoring Hardware System

There are a variety of ways the inventors developed to regulate flow of the CSF through the system. FIGS. 7-11 show several exemplary implementations. In the embodiment shown in FIG. 7, the CSF circuit 10 has four pinch valves 28 on tubing/catheters 14, enabling fluid oscillation between opposing flow directions. To flow from lumbar to ventricle (FIG. 7), pinch valves 1 and 2 are opened while pinch valves 3 and 4 are closed. Conversely, to switch flow direction from ventricle to lumbar (FIG. 8), pinch valves 1 and 2 are closed while pinch valves 3 and 4 are opened. Controlling the pinch valves 28 in this manner enables flow direction oscillation. The frequency at which the pinch valves 28 switch between open and closed may be set by the user as could the flow rate of the pump 18 (e.g., via the flow controller 22). Alternative embodiments may pre-program such parameters into the system.

In fact, the same pinch valve configuration (FIG. 9) may be used to create a pulsatile flow pattern. For example, when flowing from lumbar to ventricle, pinch valves 3 and 4 remain closed, while pinch valves 1 and 2 are pulsed (i.e., periodically switched between open and closed) at a frequency set by the user.

The ability to set the frequency at which the pinch valves 28 open and close enables a range of pulsatile effects to be implemented. For example, rather than rapidly switching between open and closed pinch valves 28, the valves 28 can remain closed long enough to build up a set pressure in the fluid line. Shortly after opening the pinch valves 28, a bolus of the drug can be released as a result of the pressure build-up.

Flow direction oscillation and a pulsatile flow pattern could also be produced using a bidirectional pump 18 instead of using pinch valves 28 (e.g., FIG. 10A and FIG. 10B). The pump 18 can be programmed to switch flow directions at a frequency set by the user. While flowing in one direction, the pump 18 can be programmed to pulse by starting and stopping at a frequency also set by the user. Those skilled in the art may use other techniques to provide bidirectional flow.

Various embodiments may set the frequency, flow rate, and other parameters as a function of the requirements and structure of the anatomy and devices used in the treatment (e.g., in the CSF circuit 10). In illustrative embodiments, the actual or calculated intracranial pressure drives the CSF flow rates. Other requirements may include the diameter of the catheters 14 in the CSF circuit 10, physical properties of the drug, the interaction of the drug at the localized region, the properties of the localized region, and other requirements and parameters relevant to the treatment. Those skilled in the art may select appropriate parameters as a function of the requisite properties.

FIG. 11 schematically shows another system interface in accordance with illustrative embodiments. Specifically, whether controlling delivery parameters by pinch valve 28, a bidirectional pump 18, or other means, the delivery profile can be controlled manually with an interface, such as the interface shown in FIG. 11, and/or a delivery profile loaded onto the system. As with the other interfaces, this interface may be a fixed control panel, a graphical user interface on a display device, or a combination of both.

As noted above and below, many of the materials, devices, and structures noted are but one of a wide variety of different materials and structures that may be used. Those skilled in the art can select the appropriate materials and structures depending upon the application and other constraints. Accordingly, discussion of specific materials, devices, and structures is not intended to limit all embodiments. Additional details are provided in the above listed patent applications that have been incorporated by reference.

In some embodiments, the management system 19/CSF circuit 10 monitors the intercranial pressure (ICP) of the patient. Specifically, as known by those in the art, a patient can become severely injured, or even die, if the intracranial pressure within the craniospinal compartment becomes too high or too low. Accordingly, to avoid discomfort or injury to the patient when accessing a patient's CSF, especially in the case where the natural CSF flow is being augmented, the ICP preferably is monitored to ensure that it does not exceed a certain high threshold pressure value (e.g., a pre-set value or calculated value on the fly), or drop below a certain low threshold pressure value (e.g., as with the high threshold, one that is pre-set or calculated on the fly). While ICP can vary widely from patient to patient, it commonly falls in the range of between 5 and 15 mm of Hg; indeed, as those in the art appreciate, ICP is dynamic and has an oscillatory nature, as it is affected by changes in the respiratory and circulatory system, and can fall outside this typical range of 5 to 15 mm of Hg. In the event of a pressure spike, for example, there is a risk of causing acute hydrocephalus. Moreover, in the event of a sudden drop in pressure, there is a risk of causing a spinal headache or in some cases severe injury and possible death if CSF were to leak out and fail to keep the brain suspended (e.g., damage to the brainstem).

Figure 12:
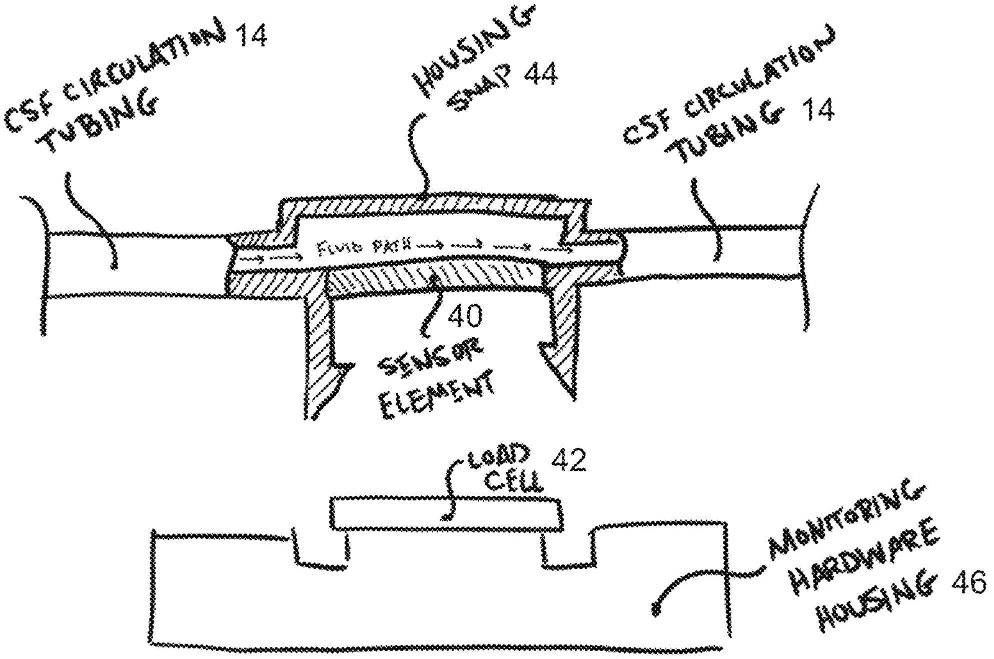
FIG. 12 schematically shows a sensor element and load cell interface coupled to CSF circulation tubing in accordance with illustrative embodiments.

To protect against such potential problems, the system/circuit 19/10 preferably has monitoring hardware comprising with at least one pressure sensor (identified by reference number "42" for this specific pressure sensor, e.g., a load cell) that is capable of measuring the ICP by connecting to a compatible component on the disposable tubing/catheter 14. This compatible component may include a sensor element 40 that is in direct contact with the CSF fluid and capable of communicating with the pressure sensor 42 (e.g., the noted load cell 42) mounted to the monitoring hardware. For example, the sensor element 40 on the tubing/catheter 14 may be in direct communication with the fluid path of a lateral ventricle, as shown in FIG. 12. FIG. 12 illustrates an embodiment of the sensor element 40 and a load cell interface 44 that are configured to attach to the tubing/catheter 14 to be in direct contact with the CSF fluid. The sensor element 40 can have a housing 46 with a downwardly extending portion to removably couple with the load cell 42 (e.g., a snap-fit). Among other things, the sensor element 40 can include a flexible diaphragm (e.g., a silicone diaphragm) that flexes in response to a pressure stimulus. As the CSF fluid flows through the CSF tubing/catheter 14, the CSF exerts an outward force on the sensor to provide a pressure signal/reading (i.e., producing data representing the pressure in the line).

The monitoring hardware may include a housing 46 with processors, memory, etc. having embedded software and a graphical user interface ("GUI"). Alternatively, in some embodiments, the GUI can be a touch screen. Obtained pressure data is collected, stored in a database, and can be displayed on the monitor where it can be observed by a clinician. The display may show 'real-time' data at various sampling frequency, average reading, minimum readings, maximum readings, etc.

In some embodiments, the system can have one or more alarms that are configured to provide alerts regarding the status of the ICP. The alarms can take into account the oscillatory nature of CSF flow by measuring the output over time. For example, in some embodiments, a first alarm may be activated if the ICP is above 20 mm of Hg for a period of 5 minutes. When this alarm is triggered, a message may be displayed instructing the clinician to check the position of the patient and confirm that the position of the sensor is approximately at the same level as the patient's ventricle. In some embodiments, a second alarm may be activated if the ICP is above 25 mm of Hg for a period of 5 minutes. When this alarm is triggered, the flow will be stopped. One method of stopping the flow may be to incorporate at least one pinch valve 28 to interface with the outer diameter of the tubing/catheter 14, as discussed above. When the alarm is triggered, the pinch valve 28 is activated and flow is stopped.

Further, a third alarm can be activated if the ICP is below 0 mm Hg for a period of 5 minutes. When this alarm is triggered, the flow will be stopped in accordance with at least one pinch valve 28 to interface with the outer diameter of the tubing/catheter 14, as discussed above. When the alarm is triggered, the pinch valve 28 is activated and flow is stopped. A person skilled in the art will recognize that one or more of the alarms can be auditory, visual, e.g., display a color such as red, green, or yellow, textual, and so forth.

Flow Controller

As noted, the system preferably includes the above discussed flow controller 22 to regulate the flow of CSF through the system as a function of the ICP. A common problem encountered in CSF aspiration and/or circulation can be one of occlusions, or significant reductions in flow such that the pressure required to achieve the desired flow rate prohibits or limits flow, which is important in flow-controlled systems. These occlusions can occur as a result of a myriad of causes, ranging from depletion of CSF from the accessed fluid compartment (e.g., lateral ventricle) to an occlusion due to collapsed anatomy (e.g., dura is drawn in, covering flow holes) to tissue (e.g., brain parenchyma) becoming lodged in the inner diameter of a catheter 14, etc.

In instances in which fluid is depleted from an accessed compartment, the potential cause of this limitation of flow could be that the systemic CSF flow rate is being driven by a pump 18, where the flow rate may be set at a rate that exceeds the rate of natural human CSF production, which is commonly reported to be in the range of 5-25 mL/hr or 0.08-0.42 mL/hr. In this scenario, the outflow of CSF from this compartment may exceed the inflow rate of newly produced CSF from the choroid plexus. Furthermore, in cases where CSF is being removed from a first location and returned to a second location, the CSF that is being returned to the second location may have insufficient time to return to the compartment of the first location and supply fluid in order to maintain patency.

Figure 13A:
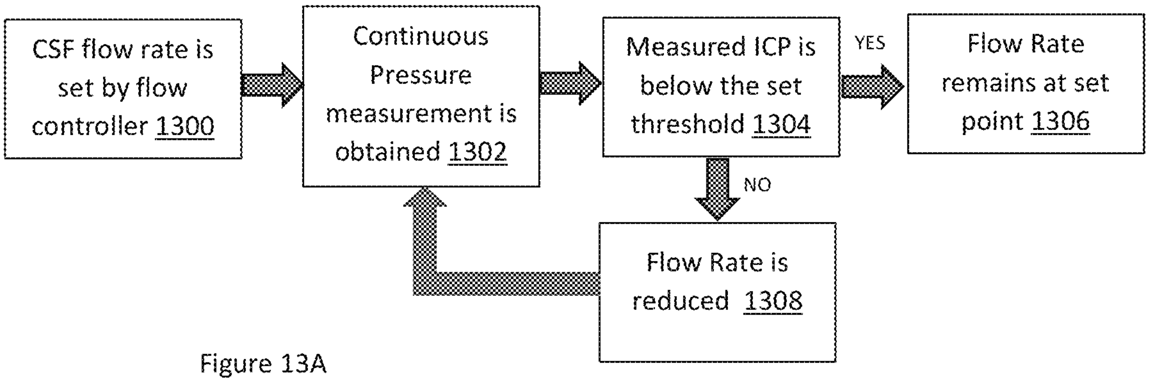
FIG. 13A provides an overview of a process involved in a closed loop flow control to maintain it with regard to a high pressure threshold value in accordance with illustrative embodiments.
Figure 13B:
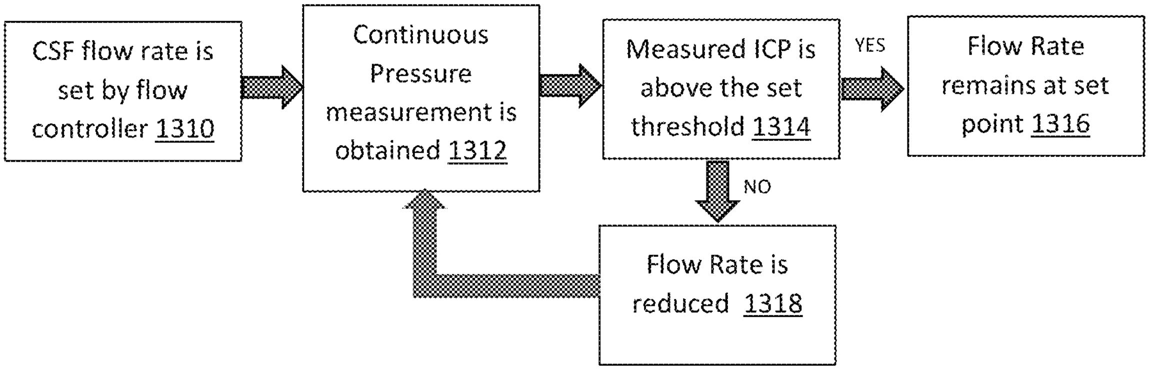
FIG. 13B provides an overview of a process involved in a closed loop flow control to maintain it with regard to a low pressure threshold value in accordance with illustrative embodiments.

FIG. 13A provides an overview of a process involved in a closed loop flow control to maintain it with regard to a high pressure threshold value in accordance with illustrative embodiments. FIG. 13B provides an overview of a process involved in a closed loop flow control to maintain it with regard to a low pressure threshold value in accordance with illustrative embodiments. Together, these processes maintain manage flow within a pressure range. It should be noted that these processes are substantially simplified from longer processes that normally would be used for closed loop flow control. Accordingly, these processes may have many additional steps that those skilled in the art likely would use. In addition, some of the steps may be performed in a different order than that shown, or at the same time. Those skilled in the art therefore can modify the processes as appropriate. Moreover, as noted above and below, many of the materials, devices, and structures noted are but one of a wide variety of different materials and structures that may be used. Those skilled in the art can select the appropriate materials and structures depending upon the application and other constraints. Accordingly, discussion of specific materials, devices, and structures is not intended to limit all embodiments.

As shown, the process of FIG. 13A begins at step 1300, in which the CSF flow rate is set by the flow controller 22. The CSF can be set at a flow rate that is based on a typical human rate of production of CSF (or the rate of CSF production for the mammal being treated), or according to another metric recognized by one skilled in the art. For example, the flow rate can be substantially constant when within a prescribed ICP range. As such, the CSF flow rate can remain substantially constant while the ICP varies between the two threshold values. Alternatively, the flow rate can vary in accordance with some underling process or reason (e.g., drug delivery) within the prescribed ICP range; i.e., the CSF flow rate can vary when within the prescribed IPC range based on variable not related to the ICP. For example, the CSF flow rate can have a first rate during a first time period, a second rate at a second time, and a third rate at a third time. Those rate(s) can be prescribed in advance (e.g., stored in a memory) and/or dictated by the dynamic information produced during the circulation process (e.g., ICP spiking in either direction).

Step 1302 therefore obtains a measurement of the ICP. In a manner similar to the CSF flow rate, the ICP can be measured continuously or periodically. When the measured ICP is below the high threshold pressure value (e.g., a prescribed or dynamically calculated value, step 1304), then the flow rate can remain constant. Conversely, when the flow rate is equal to or above the high threshold pressure value (step 1306), then the flow rate can be modified—in this case, the flow rate can be reduced by some prescribed amount. Preferably, in addition to meeting a certain high or low pressure threshold, various embodiments require that these pressure readings outside of the desired region persist for a certain amount of time (e.g., 5 minutes or some other time frame, as discussed above). This should minimize the effects of short-term pressure drops or spikes.

A similar process preferably is performed by FIG. 13B in real-time for the low threshold pressure value. Specifically, in a corresponding manner, after setting the flow rate (step 1310) and monitoring the pressure (step 1312), the pressure sensor 42 measures the ICP at step 1314. When the measured ICP is above the low threshold pressure value (e.g., a prescribed or dynamically calculated value, step 1316), then the flow rate can remain constant. Conversely, when the flow rate is equal to or below the low threshold pressure value (step 1318), then the flow rate can be modified—in this case, the flow rate can be increased by some prescribed amount.

Those skilled in the art can select appropriate high and low threshold pressure values. For example, the range can extend from 0 to 30 mm Hg, 5-25 mm Hg., or 10-25 mm Hg. Other ranges can suffice for a given application. The size of the range between the high and low threshold values, for example, can be between 5-20 mm Hg., or between 10-20 mm Hg. Other embodiments may use artificial intelligence/machine learning algorithms or other logic to calculate a dynamic ICP range and/or dynamic CSF flow rates based on the information produced by the system.

Alternative embodiments do not directly measure the ICP. In fact, the embodiment discussed above may not be considered by some to be a direct measurement. Instead, this reading may be downstream of the desired region of the craniospinal compartment and thus, provide enough information to calculate or otherwise determine the ICP. Accordingly, a direct reading is not necessary for some embodiments.

The pressure sensor 42 communicates the ICP readings directly with the controller 22, preferably in real time. This communication may be by a variety of means, such as through wireless (e.g., Bluetooth) or a direct wired connection. The controller 22 therefore accesses memory for the threshold values and/or dynamically compares the real data against the range data, which can fluctuate. When it detects that a change in CSF flow rate is needed, it may access memory having a prescribed set of change(s) to make to flow rate, or may dynamically change the flow rate based on a calculated trajectory or other logic. As another example, some embodiments may use a look-up table to determine the threshold values and/or responsive CSF flow rates. In addition to being a function of the ICP, the CSF flow rate also may be a function of other variables not discussed above, such as blood pressure, patient temperature, patient weight, prior-known patient condition (e.g., heart conditions), etc.

The flow controller 22 therefore actively monitors pressure in the line and automatically adjusts the flow rate, via the pump(s) 18 in order to maintain CSF flow, ensure a safe ICP, and aims to prevent or mitigate the likelihood of an occlusion or significant reduction in flow. For example, if the flow controller 22 is initially set to a specific flow rate and the measured pressure exceeds the high pressure threshold, the flow controller 22 can automatically reduce the flow rate, via the pump(s) 18 and/or valve(s) 28 until the pressure drops back below the set point. As noted, the in-line pressure may be actual intracranial pressure, or an indirect but correlated reading. This can enable the optimization of CSF flow without causing an occlusion. It also should be noted that the CSF flow rate may have a constant pressure at the pump output, but may vary in different parts of the CSF circuit 10. In any event, an increase in CSF flow rate typically means at least at the outlet of the pump 18 (i.e., whether it is an in-line pump 18 or a mechanical pump 18 as shown in FIG. 1B, which does not contact the CSF in the CSF circuit 10).

Accordingly, various embodiments mitigate the potentially devastating effects of ICP exceeding healthful limits. This should enable additional uses of the CSF circuit 10, including for reducing toxic proteins and/or delivering drugs to specified portions of the anatomy.

Various embodiments of the invention may be implemented at least in part in any conventional computer programming language. For example, some embodiments may be implemented in a procedural programming language (e.g., "C"), or in an object oriented programming language (e.g., "C++"). Other embodiments of the invention may be implemented as a pre-configured, stand-along hardware element and/or as preprogrammed hardware elements (e.g., application specific integrated circuits, FPGAs, and digital signal processors), or other related components.

In an alternative embodiment, the disclosed apparatus and methods (e.g., see the various flow charts described above) may be implemented as a computer program product for use with a computer system. Such implementation may include a series of computer instructions fixed either on a tangible, non-transitory medium, such as a computer readable medium (e.g., a diskette, CD-ROM, ROM, or fixed disk). The series of computer instructions can embody all or part of the functionality previously described herein with respect to the system.

Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies.

Among other ways, such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). In fact, some embodiments may be implemented in a software-as-a-service model ("SAAS") or cloud computing model. Of course, some embodiments of the invention may be implemented as a combination of both software (e.g., a computer program product) and hardware. Still other embodiments of the invention are implemented as entirely hardware, or entirely software.

The embodiments of the invention described above are intended to be merely exemplary; numerous variations and modifications will be apparent to those skilled in the art. Such variations and modifications are intended to be within the scope of the present invention as defined by any of the appended claims.

What is claimed is:

1. A CSF management system for use with a patient having a body with CSF and a port to the patient's CSF, the patient also having a craniospinal compartment, the system comprising:

a CSF circuit having a catheter, a valve, and configured to coordinate with at least one pump, the CSF circuit configured to control flow of the patient's CSF and being removably couplable with the patient's port;

a pressure sensor operably couplable with the catheter, the pressure sensor configured to monitor the intracranial pressure in the craniospinal compartment of the patient when flowing CSF through the CSF circuit; and a controller configured to control the pump to flow the CSF at a given flow rate through the CSF circuit, the controller configured to control the pump to control the given flow rate of the CSF in the CSF circuit in real time as a function of the monitored intracranial pressure in the craniospinal compartment, wherein the controller is configured to:

maintain the given flow rate at a substantially constant rate while the intracranial pressure is within a pressure threshold range defined by a high threshold pressure value and a low threshold pressure value;

automatically modify the given flow rate when the intracranial pressure is detected to be outside of the pressure threshold range to:

control the pump to reduce the given flow rate of the CSF when the intracranial pressure is detected to be equal to or greater than a high threshold pressure value; and control the pump to increase the given flow rate of the CSF when the intracranial pressure is detected to be equal to or less than the low threshold pressure value, wherein modification of the given flow rate of the CSF occurs when the intracranial pressure remains outside the pressure threshold range for a predetermined time period.

2. The system as defined by claim 1 further comprising an alarm operably coupled with the controller, the alarm configured to produce an alert when the intracranial pressure is equal to or greater than a high threshold pressure value or when the intracranial pressure is equal to or less than a low threshold pressure value.

3. The system as defined by claim 1 further comprising a display operably coupled with the controller, the display configured to produce output indicia indicating information relating to the intracranial pressure.

4. The system as defined by claim 1 the patient has a fluid port, the catheter having a removable coupling for removably coupling with the port.

5. The system as defined by claim 1 wherein the controller is configured to maintain the given flow rate at a constant rate when the intracranial pressure is between a high threshold pressure value and a low threshold pressure value.

6. The system as defined by claim 1 wherein the CSF circuit comprises a reloadable cartridge and a port for removably coupling with the reloadable cartridge, the reloadable cartridge configured to mix CSF with a material to produce a mixed CSF/material, the reloadable cartridge having an output to move the mixed CSF/material from of the reloadable cartridge and into the catheter.

7. The system as defined by claim 1 wherein the CSF circuit comprises a load cell, the controller operatively coupled with the load cell to receive a pressure signal from the load cell, the pressure signal including information relating to the intracranial pressure.

8. The system as defined by claim 1 wherein the CSF circuit comprises the pump.

* * * * *